United States Patent
Inada et al.

(10) Patent No.: US 8,624,189 B2
(45) Date of Patent: ***Jan. 7, 2014

(54) GAS MONITORING DEVICE, COMBUSTION STATE MONITORING DEVICE, SECULAR CHANGE MONITORING DEVICE, AND IMPURITY CONCENTRATION MONITORING DEVICE

(75) Inventors: Hiroshi Inada, Osaka (JP); Youichi Nagai, Osaka (JP)

(73) Assignee: Sumitomo Electric Industries, Ltd., Osaka (JP)

( * ) Notice: Subject to any disclaimer, the term of this patent is extended or adjusted under 35 U.S.C. 154(b) by 202 days.

This patent is subject to a terminal disclaimer.

(21) Appl. No.: 13/142,039

(22) PCT Filed: Jul. 30, 2009

(86) PCT No.: PCT/JP2009/063581
§ 371 (c)(1),
(2), (4) Date: Jun. 24, 2011

(87) PCT Pub. No.: WO2010/073770
PCT Pub. Date: Jul. 1, 2010

(65) Prior Publication Data
US 2011/0261359 A1    Oct. 27, 2011

(30) Foreign Application Priority Data
Dec. 25, 2008    (JP) ................................. 2008-331531

(51) Int. Cl.
*H01L 31/0248*    (2006.01)
(52) U.S. Cl.
USPC .................................................... 250/338.4
(58) Field of Classification Search
USPC .................................................... 250/338.4
See application file for complete search history.

(56) References Cited

U.S. PATENT DOCUMENTS 7,999,231 B2 *    8/2011    Iguchi et al. ............... 250/339.1
8,188,559 B2 *    5/2012    Iguchi et al. ................. 257/431
(Continued)

FOREIGN PATENT DOCUMENTS

| CN | 101021474 | 8/2007 |
| CN | 101330123 | 12/2008 |

(Continued)

OTHER PUBLICATIONS

Wu et al., "Detection of trace moisture in gases with diode laser absorption spectroscopy-Application to semiconductor manufacturing process monitoring", Journal of the Japan Society of Infrared Science and Technology 11(Jun. 2001) 33-40 (2001) with partial English translation.

(Continued)

*Primary Examiner* — Constantine Hannaher
(74) *Attorney, Agent, or Firm* — Fish & Richardson P.C.

(57) ABSTRACT

[Object] To provide a gas monitoring device etc. with which gas monitoring can be preformed at high sensitivity by using an InP-based photodiode in which a dark current is reduced without a cooling mechanism and the sensitivity is extended to a wavelength of 1.8 μm or more.

[Solution] An absorption layer 3 has a multiquantum well structure composed of group III-V semiconductors, a pn-junction 15 is formed by selectively diffusion of an impurity element in the absorption layer, and the concentration of the impurity element in the absorption layer is $5\times10^{16}/\mathrm{cm}^3$ or less. The gas monitoring device detects a gas component and the like contained in a gas by receiving light having at least one wavelength of 3 μm or less.

20 Claims, 15 Drawing Sheets

(56) References Cited

U.S. PATENT DOCUMENTS

| | | | |
|---|---|---|---|
| 8,243,139 B2* | 8/2012 | Nagai et al. | 348/148 |
| 8,373,156 B2* | 2/2013 | Nagai et al. | 257/22 |
| 2007/0246653 A1 | 10/2007 | Zhou | |
| 2007/0264835 A1 | 11/2007 | Iguchi et al. | |
| 2008/0142714 A1 | 6/2008 | Nagai et al. | |
| 2010/0051905 A1 | 3/2010 | Iguchi et al. | |

FOREIGN PATENT DOCUMENTS

| | | |
|---|---|---|
| JP | 63-1079 | 1/1988 |
| JP | 03-038887 | 2/1991 |
| JP | 05-079624 | 3/1993 |
| JP | 05-160426 | 6/1993 |
| JP | 05-160429 | 6/1993 |
| JP | 05-196220 | 8/1993 |
| JP | 09-219563 | 8/1997 |
| JP | 09-304274 | 11/1997 |
| JP | 2001-144278 | 5/2001 |
| JP | 2002-373999 | 12/2002 |
| JP | 2006-270060 | 10/2006 |
| JP | 2007-080920 | 3/2007 |
| JP | 2007-120971 | 5/2007 |
| JP | 2007-201432 | 8/2007 |
| JP | 2007-324572 | 12/2007 |
| JP | 2008-153311 | 7/2008 |
| JP | 2008-171885 | 7/2008 |
| JP | 2008-205001 | 9/2008 |
| JP | 2008-270760 | 11/2008 |
| JP | 2008-288293 | 11/2008 |
| WO | 2007/120931 | 10/2007 |

OTHER PUBLICATIONS

Yamamoto et al., "Optical properties of $GaAs_{0.5}Sb_{0.5}$ and $In_{0.53}Ga_{0.47}As/GaAs_{0.5}Sb_{0.5}$ type II single hetero-structures lattice-matched to InP substrates grown by molecular beam epitaxy," J. of Crystal Growth, Elsevier 201/202, pp. 872-876 (1999).

Nakayama, M., "Technology trend of infrared detecting elements", Hamamatsu Photonics K.K., 9(3): 61-64 (Mar. 1989) with partial English translation.

Sidhu et al., "A Long-Wavelength Photodiode on InP Using Lattice Matched GaInAs-GaAsSb Type-II Quantum Wells," IEEE Photonics Tech. Letters 17(12):2715-2717 (2005).

The State Intellectual Property Office of the People's Republic of China, Notification of the second office action dated to the corresponding CN Patent Application No. 200980152617.2, and its English translation (Sep. 29, 2013).

* cited by examiner

GAS MONITORING DEVICE, COMBUSTION STATE MONITORING DEVICE, SECULAR CHANGE MONITORING DEVICE, AND IMPURITY CONCENTRATION MONITORING DEVICE

TECHNICAL FIELD

The present invention relates to a gas monitoring device, a combustion state monitoring device, a secular change monitoring device, and an impurity concentration monitoring device that monitor a gas component and the like (a gas component, flotage such as soot, and the like) contained in a gas in an industrial apparatus or an infrastructure facility such as a combustor by using a semiconductor light-receiving element having sensitivity to light including the near-infrared region.

BACKGROUND ART

In facilities such as a boiler, a combustor, and the like, the state of a flame or gas that changes in accordance with the operation condition is detected, the detection results are reflected in the operation, and in addition, the degradation state of the facilities is examined to maintain the upkeep of the facilities. Since gases allow electromagnetic waves to pass therethrough more easily than solids, gases are suitable for optical monitoring. In particular, light in the near-infrared region is suitable for monitoring a gas generated from an organic substance because an absorption spectrum of a gas of a hydrocarbon or the like is located in the near-infrared region. However, in analysis by near-infrared spectroscopy, an output signal includes a large amount of noise due to a light-receiving element. Therefore, in order to extract necessary information regarding an output signal without totally depending on an improvement of the performance of sensors (light-receiving elements), a spectroscopic method, chemometrics, or the like has been used as an important method.

In the near-infrared region, the above-mentioned sensors (light-receiving elements) are broadly divided into electron tubes and photodiodes (PDs) which are solid-state components. Among these sensors, PDs have a small size and can be easily highly integrated to form a one-dimensional array, a two-dimensional array, or the like, and thus research and development of PDs has been widely performed (Non-Patent Literature (NPL) 1). The present invention targets a detection device for biological components, the detection device including a PD. Currently, the following PDs or PD arrays are used. (1) An example of such PDs or PD arrays is PDs or arrays thereof having sensitivity up to the infrared region and also having sensitivity in the near-infrared region. Specific examples of such PDs include germanium (Ge)-based PDs, lead sulfide (PbS)-based PDs, HgCdTe-based PDs, one-dimensional arrays thereof, and two-dimensional arrays thereof. (2) Another example of such PDs or PD arrays is InP-based PDs having sensitivity at a wavelength of 1.7 μm or less in the near-infrared region, InGaAs-based PDs included in the category of the InP-based PDs, and arrays thereof. Herein, the InP-based PDs refer to PDs including an absorption layer composed of a group III-V compound semiconductor and formed on an InP substrate, and InGaAs-based PDs are also included in the InP-based PDs.

Among the above photodiodes, photodiodes described in (1) are often cooled in order to reduce noise. For example, most of the photodiodes are operated while cooling at the liquid nitrogen temperature (77 K) or while cooling with a Peltier device. Accordingly, devices including such photodiodes have a large size, and the device cost is increased. Although such devices can be used at room temperature, the devices have a problem that a dark current is high in the wavelength range of 2.5 μm or less and the detection capability is poor. On the other hand, the InP-based PDs described in (2) have the following disadvantages: (I) In InGaAs, which is lattice-matched to InP, although a dark current is low, the sensitivity of the PD is limited to a wavelength range of 1.7 μm or less in the near-infrared region. (II) In extended-InGaAs, in which the wavelength region where light can be received is extended to 2.6 μm, the dark current is high, and cooling is necessary. Accordingly, in the InP-based PDs, light having a wavelength of 2.0 μm or more, which is important for improving the accuracy in gas monitoring, cannot be used or it is necessary to cool the PDs in order to use the light.

With regard to an example of optical monitoring using near-infrared light, in the maintenance of an oil-filled instrument containing insulating oil therein, such as an oil-filled (OF) cable, the degradation of the oil-filled instrument is examined by detecting the composition ratio of a plurality of hydrocarbons contained in a gas dissolved in the oil (Patent Literature (PTL) 1 and PTL 2). In particular, PTL 2 proposes a device configured to detect the concentration of a hydrocarbon gas and the concentration of hydrogen, which has no absorption spectrum in the infrared region due to the diatomic molecule thereof. In this optical monitoring device, a light-receiving element having sensitivity in a wavelength range of 1.5 to 1.6 μm is used.

As another example, in order to suppress the generation of nitrogen oxides, soot, and carbon monoxide in a combustion device such as a boiler, an optical monitoring device configured to monitor a combustion state has been proposed (PTL 3). In this device, a multilayer light-receiving element in which a silicon photodiode and a PbS photoconductive element are stacked is used. In addition, a multilayer light-receiving element including a silicon photodiode and a Ge photodiode in combination, and a multilayered light-receiving element including a silicon photodiode and a PbSe photoconductive element in combination have also been proposed. The reason why a silicon photodiode is used is to receive light having a wavelength in the visible light region or light having a wavelength near the visible light region.

Furthermore, an infrared camera that detects the temperature distribution of the entire part of an incinerator in a combustor has been proposed (PTL 4). The content of a light-receiving portion of this infrared camera is not known.

In a manufacturing process of a large-scale integrated circuit (LSI) or the like, high-purity gases are used in deposition of epitaxial films. However, these gases contain trace moisture, which adversely affects durability of the LSI or the like. To monitor such trace moisture contained in a gas, a device configured to receive transmitted light of the gas using a laser light source that oscillates at a single wavelength in the near-infrared region, and to detect a moisture concentration on the order of 0.1 to 1 ppm by lock-in detection has been proposed (NPL 2). A germanium photodiode is used as a light-receiving element in this device.

In the light-receiving devices for detecting a gas component and other general near-infrared light-receiving devices, a single element or an array of elements of InGaAs, PbS, Ge, HgCdTe, an extended-InGaAs including multistage step buffer layers, or the like is used. A light-receiving wavelength range common to all the above-mentioned gas monitoring devices is 1 to 1.8 μm. However, some of the devices determine the upper limit of the light-receiving wavelength range to about 2.0 μm or 2.5 μm.

As described above, as for InGaAs, it is necessary to extend the sensitivity to the long-wavelength side of the near-infrared region. To improve the sensitivity, the methods below have been proposed.

(K1) The indium (In) proportion of an InGaAs absorption layer is increased, and lattice mismatching between the absorption layer and an InP substrate is absorbed by interposing step buffer layers, in which the In proportion is changed stepwise, therebetween (PTL 5).

(K2) Nitrogen (N) is incorporated in an InGaAs absorption layer to form a GaInNAs absorption layer (PTL 6). Lattice matching with an InP substrate is satisfied by incorporating a large amount of N.

(K3) An extension of the light-receiving wavelength range to the long-wavelength side is realized by providing a type-II multiquantum well structure composed of GaAsSb and InGaAs (NPL 3). Lattice matching with an InP substrate is satisfied.

(K4) Formation of a two-dimensional array is realized by forming element separation trenches between light-receiving elements (pixels) by wet etching (PTL 7).

NPL 1: Masao Nakayama "Technology trend of infrared detecting elements", Sensor Technology, 1989 March issue (Vol. 9, No. 3), p. 61-64

NPL 2: Shang-Qian Wu, et al., "Detection of trace moisture in gas with diode laser absorption spectroscopy", Journal of the Japan Society of Infrared Science and Technology, Vol. 11, p. 33-40 (2001)

NPL 3: R. Sidhu, "A Long-Wavelength Photodiode on InP Using Lattice-Matched GaInAs—GaAsSb Type-II Quantum Wells", IEEE Photonics Technology Letters, Vol. 17, No. 12 (2005), pp. 2715-2717

PTL 1: Japanese Unexamined Patent Application Publication No. 2007-120971

PTL 2: Japanese Unexamined Patent Application Publication No. 09-304274

PTL 3: Japanese Unexamined Patent Application Publication No. 05-79624

PTL 4: Japanese Unexamined Patent Application Publication No. 05-196220

PTL 5: Japanese Unexamined Patent Application Publication No. 2002-373999

PTL 6: Japanese Unexamined Patent Application Publication No. 9-219563

PTL 7: Japanese Unexamined Patent Application Publication No. 2001-144278

DISCLOSURE OF INVENTION

Technical Problem

In the light-receiving elements described above, in summary, elements have been proposed in which near-infrared light having a wavelength up to a maximum of 2,500 nm is used. The upper limit of the wavelength is preferably large so long as the sensitivity is good because a large amount of information can be obtained. However, in order to receive light having a wavelength exceeding 1.7 µm using a light-receiving element including PbS, HgCdTe, or the like, as described above, it is necessary to solve problems such as a high dark current and a low detection capability, and to enhance the detection resolution. Furthermore, in the case where such a light-receiving element is used while cooling in order to enhance the detection capability, the gas monitoring device has a large size.

Although an InGaAs light-receiving element that is lattice-matched to an InP substrate is excellent in terms of detection capability, the wavelength corresponding to the sensitivity of the element is 1.7 µm or less. Accordingly, this light-receiving element is not suitable for detecting, for example, gas components which have a large number of absorption spectra in a wavelength range longer than this. In particular, as in hydrocarbon gases generated from an organic substance, in the case where a large number of components are mixed, in order to improve the resolution, it is desirable to comprehensively detect a single gas component, which is a detection target, using two or more absorption bands attributable to the gas component. However, in such a detection of a gas component using two or more absorption bands, a sensitivity wavelength range of 1.7 µm or less is very insufficient.

Meanwhile, as described in the methods (K1) to (K4) above, there are some candidates for a light-receiving element and a light-receiving element array that do not require cooling and that have sensitivity at the long-wavelength side of the near-infrared region. However, the candidates each have the following problems.

(K1): Since the InP substrate and the absorption layer are not completely lattice-matched to each other, a dark current due to a high lattice defect density is very high. Accordingly, a sufficiently high dynamic range (SN ratio) cannot be achieved, and noise is high. Consequently, the number of dark spots (image omissions) increases.

In addition, in order to realize lattice matching, InP cannot be used as a window layer constituting a top layer of a laminate, and it is necessary to provide an InAsP window layer. Consequently, the sensitivity in a range from the near-infrared region to the shorter wavelength side, in which important absorption bands are located in some biological components, decreases.

(K2): When the amount of N is about 10 atomic percent in order to extend the bandgap wavelength to the longer wavelength side while achieving lattice matching to InP, it is very difficult to obtain GaInNAs composed of good crystals. Furthermore, it is very difficult and almost impossible to obtain GaInNAs having a thickness of about 2 µm in order to sufficiently increase the sensitivity. That is, sharp images cannot be obtained.

(K3): When an impurity is introduced into an absorption layer having a multiquantum well structure by an ordinary method, the crystal quality of the multiquantum well structure is degraded. Consequently, the production yield decreases, thereby increasing the product cost, and a good crystal quality is not easily obtained. Accordingly, although the light-receiving wavelength range can be extended to a longer wavelength of about 2.5 µm, sharp images cannot be obtained.

(K4): In order to form an array by means of element separation by wet etching, it is necessary that an etchant enter trenches sufficiently deeply and uniformly. However, the etchant does not enter the trenches sufficiently deeply and uniformly and such a control is difficult. Consequently, the production yield decreases. On the other hand, when dry etching is employed, light-receiving elements are damaged. In particular, in the case of a device that receives light diffracted in accordance with the wavelength, e.g., a gas monitoring device, the above damage cannot be accepted.

If near-infrared spectroscopy can be easily performed with high sensitivity using a photodiode in which the dark current is suppressed without using a cooling mechanism, a trace gas component and a very small amount of temperature change can be detected also in gas monitoring, and thus usability can be increased.

An object of the present invention is to provide a gas monitoring device capable of performing gas monitoring with high sensitivity by using an InP-based photodiode in which the dark current is reduced without providing a cooling mechanism and the sensitivity is extended to a wavelength of 1.8 μm or more, a combustion state monitoring device, a secular change monitoring device, and an impurity concentration monitoring device that include the gas monitoring device.

Solution to Problem

A gas monitoring device of the present invention is a device for monitoring a gas using light in the near-infrared region with a wavelength range of 3 μm or less. The gas monitoring device includes a light-receiving element that receives light in the near-infrared region, and the light-receiving element includes an absorption layer formed on an InP substrate and having a multiquantum well structure. The absorption layer has a bandgap wavelength of 1.8 μm or more and 3 μm or less, and a diffusion concentration distribution control layer is disposed on a surface side of the absorption layer, the surface side being opposite the InP substrate. The diffusion concentration distribution control layer has a bandgap smaller than that of InP. In the light-receiving element, a pn-junction is formed by selectively diffusing an impurity element through the diffusion concentration distribution control layer so as to reach the absorption layer. The concentration of the impurity element in the absorption layer is $5 \times 10^{16}/cm^3$ or less. The light-receiving element receives light from the gas, the light having at least one wavelength of 3 μm or less, to detect a gas component and the like (a gas component, flotage such as fine particles, and the like) contained in the gas.

According to the above configuration, by lowering the concentration of the impurity element to be $5 \times 10^{16}$ cm$^{-3}$ or less, a multiquantum well structure having a bandgap energy corresponding to the near-infrared region can be formed without breaking the multiquantum well structure, that is, without impairing the crystal quality. Furthermore, the impurity for forming the pn-junction of the light-receiving element is selectively diffused, that is, the impurity is introduced into the inside of the peripheral portion of the light-receiving element by diffusion so that the diffusion in the peripheral portion is two-dimensionally limited. Thus, the impurity is introduced so that the light-receiving elements are separated from each other. Accordingly, each of the light-receiving elements can be easily formed with high accuracy, and element separation trenches need not be provided. Thus, light-receiving elements having a low dark current can be formed. Consequently, light can be received with high sensitivity without cooling in a wavelength of 3 μm or less. There are several absorption bands of a gas component (molecule) contained in a gas in a wavelength range of 0.9 to 3 μm. Therefore, detection can be performed with the above gas monitoring device using the plurality of absorption bands at the same time. Thus, the detection accuracy can be improved.

By controlling the bandgap of the diffusion concentration distribution control layer to be smaller than that of InP, even when the concentration of the impurity element in a thickness range at the absorption layer side of the diffusion concentration distribution control layer is decreased, the electrical resistance can be suppressed to be low. Thus, a decrease in the response time can be prevented. More specifically, the reasons why the bandgap of the diffusion concentration distribution control layer is controlled to be smaller than the bandgap of the InP substrate are as follows:

(1) When an absorption layer for the near-infrared region is formed of group III-V compound semiconductors, a material having a bandgap energy larger than the bandgap energy of the absorption layer is used as a window layer in some cases. In such a case, the same material as the semiconductor substrate is often used as the window layer in consideration of lattice matching and the like. It is assumed that the bandgap energy of the diffusion concentration distribution control layer is smaller than the bandgap energy of the window layer and larger than the bandgap energy of the absorption layer. This is because, if the bandgap energy of the diffusion concentration distribution control layer is smaller than the bandgap energy of the absorption layer and a structure in which the top surface of an epitaxial layer functions as an incident surface is adopted, the diffusion concentration distribution control layer absorbs light that should be absorbed by the absorption layer, thereby decreasing sensitivity of the absorption layer.

(2) By using a material having a bandgap energy smaller than a large bandgap energy of a material that is usually used as a window layer, even when the impurity concentration is reduced, it is possible to suppress an increase in the electrical resistance or a decrease in the electrical conductivity. As a result, as described above, a decrease in a response time can be suppressed in a voltage-applied state.

Here, "detection" may refer to a case where calibration curve of a predetermined component (a relationship between the concentration of the predetermined component and the intensity or absorbance of light at the wavelength) is prepared in advance, and the concentration or the content of the predetermined component is determined. Alternatively, "detection" may refer to a method in which such a calibration curve is not used. Note that the above pn-junction should be broadly interpreted as follows. In the absorption layer, when a region on a surface side opposite a surface from which the impurity element is introduced by selective diffusion is an impurity region (also referred to as "i region") in which the impurity concentration is low enough for the impurity region to be considered as an intrinsic semiconductor, a junction formed between this i-region and the impurity region formed by the selective diffusion is also included in the pn-junction. That is, the pn-junction mentioned above may be a pi-junction, an ni-junction, or the like. Furthermore, the pn-junction also includes the case where the p concentration in the pi-junction or the n concentration in the ni-junction is very low.

In the diffusion concentration distribution control layer, the distribution of the concentration of the impurity element may decrease from a high concentration of about $1 \times 10^{18}/cm^3$ or more on the side opposite the absorption layer to $5 \times 10^{16}/cm^3$ or less on the absorption layer side. In this case, a good crystal quality of the multiquantum well structure can be ensured while reducing the interface resistance of an electrode disposed on the top surface side or allowing an ohmic contact of the electrode to be formed. The problem of an increase in the electrical resistance or a decrease in the electrical conductivity due to a low impurity concentration in a portion in the diffusion concentration distribution control layer can be reduced by controlling the bandgap energy of the diffusion concentration distribution control layer to be smaller than the bandgap energy corresponding to that of InP, as described above.

The absorption layer may have a type II quantum well structure. In this case, in absorption of electromagnetic waves, transition of electrons from a layer of a high valence band to a layer of a low conduction band can be performed. Thus, sensitivity to light in the longer wavelength range can be easily obtained.

The absorption layer may have a multiquantum well structure composed of (InGaAs/GaAsSb) or a multiquantum well structure composed of (GaInNAs (P, Sb)/GaAsSb). Herein, (GaInNAs (P, Sb)/GaAsSb) means (GaInNAsP/GaAsSb), (GaInNAsSb)/GaAsSb), (GaInNAsPSb)/GaAsSb), or (GaInNAs/GaAsSb). In this case, a light-receiving element having a good crystal quality and a low dark current can be easily obtained by using materials and techniques that have been accumulated to date.

The InP substrate may be an off-angle substrate which is tilted at 5° to 20° from (100) in the [111] direction or the [11-1] direction. In this case, it is possible to obtain a laminate including an absorption layer having a multiquantum well structure in which the defect density is low and which has a good crystal quality. Consequently, it is possible to obtain an absorption layer in which a dark current is suppressed and the number of dark spots is small.

The impurity element may be zinc (Zn), and the diffusion concentration distribution control layer may be composed of InGaAs. In this case, the diffusion concentration distribution control layer can be formed of a material for which the dependency of the electrical resistance on the impurity concentration is small, the material having an electrical resistance which does not significantly increase even at a low impurity concentration. Suppressing an increase in the electrical resistance prevents the degradation of the response time. In addition, zinc used as the impurity has been widely used in selective diffusion to date, and can form a diffusion region with high accuracy. Accordingly, it is possible to prevent an increase in the electrical resistance on the lower side of the diffusion concentration distribution control layer while the impurity concentration which is high at the upper side, i.e., the diffusion introduction side is decreased toward the lower side, i.e., the absorption layer side in the diffusion concentration distribution control layer. Therefore, it is possible to prevent a region having a high impurity concentration from being formed in the absorption layer having a quantum well structure. As a result, a light-receiving element having a quantum well structure with a good crystal quality can be obtained without decreasing responsiveness. Note that the bandgap energy of InGaAs is 0.75 eV.

An InP window layer may be provided on the diffusion concentration distribution control layer. The formation of the window layer composed of InP does not decrease the crystal quality of the semiconductor stacked structure disposed inside. Accordingly, when a structure in which an epitaxial layer is disposed on the incident surface side is adopted, the InP window layer also effectively acts to suppress the dark current while preventing, for example, absorption of near-infrared light at a position closer to the incident side than the absorption layer. Furthermore, techniques for forming a passivation film on a crystal surface of InP have been accumulated and technically established, as compared with techniques for forming a passivation film on other crystal surfaces, for example, techniques for forming a passivation film on a surface of InGaAs. Accordingly, a current leakage on the surface can be easily suppressed.

In any two of the InP substrate, respective layers constituting the quantum well structure of the absorption layer, and the diffusion concentration distribution control layer, lattice matching ($|\Delta a/$'a'$|$: where 'a' represents a lattice parameter and $\Delta a$ represents a difference in the lattice parameter between the two) may be 0.002 or less. With this configuration, an absorption layer having a good crystal quality can be obtained by using an InP substrate that is commonly available. Accordingly, in a light-receiving element or light-receiving element array of near-infrared light having a wavelength of 1.8 µm or more, the dark current can be significantly suppressed.

A plurality of the light-receiving elements may be one-dimensionally or two-dimensionally arrayed. In the light-receiving element array, a plurality of the light-receiving elements include a semiconductor stacked structure in common, the impurity element is introduced by selective diffusion in the absorption layer for each of the light-receiving elements, and the light-receiving elements are arranged one-dimensionally or two-dimensionally. According to this configuration, since the light-receiving elements are formed in individual impurity diffusion regions, element separation trenches need not be provided. Therefore, it is possible to form a light-receiving element array which is easily formed with high accuracy, and in which the dark current can be reduced.

The gas monitoring device may include a two-dimensional array of the light-receiving elements, and images of the concentration distribution and the temperature distribution of the gas component in the gas may be formed with the imaging device. In this case, it is possible to obtain distribution images of a predetermined component contained in the target object, the distribution image being easily understood visually.

In the light-receiving element, the epitaxial layer top side that is opposite the InP substrate side with the absorption layer therebetween may function as a light-incident surface, or the InP substrate side may function as the light-incident surface and the InP substrate may be removed or the thickness of the InP substrate may be reduced to the same thickness as that of the absorption layer or less. In this case, it is possible to prevent light in the visible region to the near-infrared region from being absorbed by the InP substrate, and to improve the sensitivity at wavelengths shorter than those of the near-infrared region. As a result, the color of light emitted from a flame, garbage during combustion, soot, a colored sensor, or the like can be monitored, and extension of the detected content and an improvement of the detection accuracy can be realized. With regard to light from the gas, an absorption spectrum and/or an emission spectrum of a gas component and the like (a gas component, flotage in the gas, and the like) can be monitored. Accordingly, in addition to the concentration of the gas component, the temperature of the gas or the like can be monitored.

A combustion state monitoring device of the present invention includes any one of the above-described gas monitoring devices, in which a combustion state of a substance such as a fuel or garbage is monitored. With this configuration, an appropriate combustion state can be maintained while suppressing the generation of a harmful gas such as $NO_x$, for example.

A secular change monitoring device of the present invention includes any one of the above-described gas monitoring devices, in which a gas component that is generated with a secular change in an instrument is monitored. With this configuration, for example, secular degradation of an OF cable for electrical power transmission can be detected to prevent the occurrence of an accident.

An impurity concentration monitoring device of the present invention includes any one of the above-described gas monitoring devices, in which the concentration of a gas component of impurities contained in a gas introduced from the outside is monitored. With this configuration, for example, in semiconductor manufacturing using high-purity process gases, trace harmful impurities such as moisture are monitored, and thus a prompt action can be taken. As a result, the quality of the resulting products can be maintained.

Advantageous Effects of Invention

According to the gas monitoring device of the present invention and the combustion state monitoring device including the gas monitoring device etc., a gas component contained in a gas can be detected with high sensitivity by using an InP-based light-receiving element in which the dark current is reduced without providing a cooling mechanism and the sensitivity is extended to a wavelength of 1.8 µm or more.

BEST MODES FOR CARRYING OUT THE INVENTION (Embodiment 1 - Structure of Semiconductor Light-receiving Element Array)

FIG. 1 is a cross-sectional view showing a light-receiving element 10 according to an embodiment of the present invention. Referring to FIG. 1, the light-receiving element 10 includes a group III-V semiconductor stacked structure (epitaxial wafer) disposed on an InP substrate 1 and having the following structure.

(InP Substrate 1/InP Buffer Layer 2/Absorption Layer 3 Having a Multiquantum Well Structure Composed of InGaAs or GaInNAs and GaAsSb/InGaAs Diffusion Concentration Distribution Control Layer 4/InP Window Layer 5)

A p-type region 6 extending from the InP window layer 5 to the absorption layer 3 having the multiquantum well structure is formed by selectively diffusing Zn, which is a p-type impurity, from an opening of a selective diffusion mask pattern 36 composed of a SiN film. By performing diffusion using the selective diffusion mask pattern 36 composed of the SiN film, the p-type impurity can be introduced into the inside of the peripheral portion of the light-receiving element 10 by diffusion so that the diffusion in the peripheral portion is two-dimensionally limited.

A p-side electrode 11 composed of AuZn and an n-side electrode 12 composed of AuGeNi are provided on the p-type region 6 and the reverse face of the InP substrate 1, respectively, so as to form an ohmic contact. In this case, the InP substrate 1 is doped with an n-type impurity so as to have an electrical conductivity at a predetermined level. An anti-reflection film 35 composed of SiON is also provided on the reverse face of the InP substrate 1 so that the light-receiving element 10 can also be used when light is incident from the reverse face side of the InP substrate.

A pn-junction is formed in the absorption layer 3 having the multiquantum well structure at a position corresponding to a boundary front of the p-type region 6. By applying a reverse bias voltage between the p-side electrode 11 and the n-side electrode 12, a depletion layer is more widely generated on the side in which the n-type impurity concentration is low (n-type impurity background). The background in the absorption layer 3 having the multiquantum well structure has an n-type impurity concentration (carrier concentration) of about $5\times10^{15}/cm^3$ or less. The position 15 of the pn-junction is determined by an intersection between the background (n-type carrier concentration) of the absorption layer 3 having the multiquantum well and a concentration profile of Zn serving as a p-type impurity. That is, the pn-junction 15 is located at the position shown in FIG. 2.

In the diffusion concentration distribution control layer 4, the concentration of the p-type impurity that is selectively diffused from a surface 5a of the InP window layer 5 drastically decreases from a high-concentration region at the InP window layer side to the absorption layer side. Accordingly, in the absorption layer 3, a Zn concentration of $5\times10^{16}/cm^3$ or less can be easily realized as an impurity concentration. In FIG. 2, a lower Zn concentration of about $1\times10^{16}/cm^3$ or less is realized in the absorption layer 3.

Since the light-receiving element 10 targeted by the present invention aims to have sensitivity in the range from the near-infrared region to the long-wavelength side thereof, the window layer is preferably composed of a material having a bandgap energy larger than the bandgap energy of the absorption layer 3. For this reason, InP, which is a material having a bandgap energy larger than that of the absorption layer and having good lattice matching, is usually used as the window layer. Alternatively, InAlAs, which has a bandgap energy substantially the same as that of InP, may also be used.

(Points of Light-receiving Element Array of this Embodiment)

Features of this embodiment lie in that the following factors are included.

1. When a high concentration of an impurity is introduced into a multiquantum well structure by selective diffusion, the multiquantum well structure is broken. Therefore, it is necessary to suppress the amount of impurity introduced by the selective diffusion to be low. In general, it is necessary to control the concentration of the p-type impurity introduced by diffusion to be $5\times10^{16}/cm^3$ or less.

2. In order to stably achieve the above-mentioned low concentration of the p-type impurity with a good repeatability in the actual production, the diffusion concentration distribution control layer 4 composed of InGaAs is provided on the absorption layer 3. If, in the diffusion concentration distribution control layer 4, a thickness range at the absorption layer side has the above-mentioned low impurity concentration, the electrical conduction property in the low-impurity concentration range decreases or the electrical resistance in the low-impurity concentration range increases. When the electrical conduction property of the low-impurity concentration range in the diffusion concentration distribution control layer 4 decreases, the responsiveness decreases, and, for example, good moving images cannot be obtained. However, in the case where the diffusion concentration distribution control layer is formed of a material having a bandgap energy smaller than the bandgap energy corresponding to that of InP, specifically, a group III-V semiconductor material having a bandgap energy less than 1.34 eV, even if the impurity concentration is low, the electrical conduction property does not very significantly decrease. An example of the group III-V semiconductor material that satisfies the above requirement of the diffusion concentration distribution control layer is InGaAs.

The reason why the impurity concentration of the absorption layer is controlled to be $5\times10^{16}/cm^3$ or less will be described in more detail. If the Zn concentration in the absorption layer 3 exceeds $1\times10^{17}$ $cm^{-3}$ because, for example, the depth of the selective diffusion of the p-type impurity (Zn) is increased, in the resulting high-concentration portion having a Zn concentration of more than $1\times10^{17}$ $cm^{-3}$, atoms of InGaAs and GaAsSb constituting the quantum well layers are disordered to each other, whereby a superlattice structure is broken. The crystal quality of the broken portion degrades, thereby degrading characteristics of the element, for example, increasing the dark current. Here, the Zn concentration is usually measured by secondary ion mass spectroscopy (SIMS). However, it is difficult to analyze a concentration on the order of $10^{17}$ $cm^{-3}$ or $10^{16}$ $cm^{-3}$, and a relatively large measurement error is generated. The above detailed description concerns a discussion about the values of the Zn concentration with a double or half accuracy, and this is resulted from this roughness of the measurement accuracy. Accordingly, for example, discussing a difference between $5\times10^{16}/cm^3$ and $6\times10^{16}/cm^3$ is difficult because of the low measurement accuracy, and is not so significant.

By using a material having a narrow bandgap energy as the diffusion concentration distribution control layer, an increase in the electrical resistance can be suppressed even at a low impurity concentration. It is believed that the response time to the application of a reverse bias voltage or the like is determined by the CR time constant determined by the capacitance and the electrical resistance. Accordingly, the response time can be shortened by suppressing the increase in the electrical resistance R as described above.

3. In this embodiment, the multiquantum well structure has a type-II structure. In a type-I quantum well structure, in the case of a light-receiving element having a structure in which a semiconductor layer having a small bandgap energy is sandwiched between semiconductor layers having a large bandgap energy so as to provide sensitivity in the near-infrared region, the upper limit of the wavelength (cutoff wavelength) of the sensitivity is determined by the bandgap of the semiconductor layer having the small bandgap energy. That is, the transition of electrons or holes caused by light is performed in the semiconductor layer having the small bandgap energy (direct transition). In this case, a material that extends the cutoff wavelength to a longer-wavelength range is very limited among group III-V compound semiconductors. In contrast, in the type-II quantum well structure, when two different types of semiconductor layers having the same Fermi energy are alternately stacked, an energy difference between the conduction band of a first semiconductor and the valence band of a second semiconductor determines the upper limit of the wavelength (cutoff wavelength) of the sensitivity. That is, the transition of electrons or holes caused by light is performed between the valence band of the second semiconductor and the conduction band of the first semiconductor (indirect transition). Therefore, by controlling the energy of the valence band of the second semiconductor to be higher than the energy of the valence band of the first semiconductor, and controlling the energy of the conduction band of the first semiconductor to be lower than the energy of the conduction band of the second semiconductor, the sensitivity can be easily extended to the long-wavelength side, as compared with the case of the direct transition performed in a single semiconductor.

4. As described above, the p-type impurity is introduced into the inside of the peripheral portion of the light-receiving element by diffusion so that the diffusion in the peripheral portion is two-dimensionally limited by performing selective diffusion using the selective diffusion mask pattern. Accordingly, the pn-junction described above is not exposed on the edges of the light-receiving element. As a result, leakage of a photocurrent is suppressed.

FIG. 3 is a cross-sectional view showing a light-receiving element array 50 in which a plurality of the light-receiving elements 10 described above are arranged on an epitaxial wafer including a common InP substrate. A feature of this light-receiving element array 50 lies in that the plurality of light-receiving elements 10 are arranged without element separation trenches. As described in item 4 above, a p-type region 6 is limited inside each of the light-receiving elements, and is reliably separated from adjacent light-receiving elements. An absorption layer 3 is formed so as to have a multiquantum well structure, a diffusion concentration distribution control layer 4 is arranged on the absorption layer 3, and the p-type impurity concentration in the absorption layer 3 is controlled to be $5 \times 10^{16}/cm^3$ or less. These points etc. are the same as those of the light-receiving element 10 shown in FIG. 1.

Next, a method for producing the light-receiving element 10 shown in FIG. 1 will be described. An InP buffer layer 2 or InGaAs buffer layer 2 having a thickness of 2 μm is deposited on an n-type InP substrate 1. Subsequently, an absorption layer 3 having a multiquantum well structure composed of (InGaAs/GaAsSb) or (GaInNAs/GaAsSb) is formed. The thickness of the InGaAs layer (or the GaInNAs layer) forming a unit quantum well structure is 5 nm, and the number of pairs (the number of repetitions of the unit quantum well) is 300. Subsequently, as a diffusion concentration distribution control layer 4, which functions in the introduction of Zn by diffusion, an InGaAs layer having a thickness of 1 μm is epitaxially grown on the absorption layer 3. Lastly, an InP window layer 5 having a thickness of 1 μm is then epitaxially grown. Both the absorption layer 3 and the diffusion concentration distribution control layer 4 are preferably epitaxially grown by a molecular beam epitaxy (MBE) method. The InP window layer 5 may be epitaxially grown by the MBE method. Alternatively, the InP substrate 1 may be taken out from an MBE apparatus after the growth of the diffusion concentration control layer 4, and the InP window layer 5 may be epitaxially grown by a metal organic vapor phase epitaxy (MOVPE) method.

The InP buffer layer 2 or the InGaAs buffer layer 2 may be non-doped or may be doped with an n-type dopant such as silicon (Si) in a concentration of about $1 \times 10^{17}/cm^3$. The absorption layer 3 having the multiquantum well structure composed of InGaAs/GaAsSb (or GaInNAs/GaAsSb), the diffusion concentration distribution control layer 4 composed of InGaAs, and the InP window layer 5 are preferably non-doped. However, these layers may be doped with a trace amount (for example, about $2 \times 10^{15}/cm^3$) of an n-type dopant such as Si. Furthermore, a high-concentration n-side electrode formation layer for forming an n-side electrode, the n-side electrode formation layer being doped with an n-type dopant of about $1 \times 10^{18}$ cm$^{-3}$, may be interposed between the InP substrate 1 and the buffer layer 2. The InP substrate 1 may be an Fe-doped semi-insulating InP substrate. In this case, the n-side electrode formation layer doped with the n-type dopant of about $1 \times 10^{18}/cm^3$ is interposed between the semi-insulating InP substrate 1 and the buffer layer 2.

An optical device is produced using the stacked structure (epitaxial wafer) including the InP substrate 1 described above. Selective diffusion of Zn is performed from an opening of a SiN mask pattern 36 formed on a surface 5a of the InP window layer 5. Thus, a p-type region 6 is formed so as to extend in the absorption layer 3 having the InGaAs/GaAsSb (or GaInNAs/GaAsSb) multiquantum well structure. A front end portion of the p-type region 6 forms a pn-junction 15. In this case, a high-concentration region having a Zn concentration of about $1 \times 10^{18}/cm^3$ or more is limited in the InGaAs diffusion concentration distribution control layer 4. That is, the above high-concentration impurity distribution continues from the surface 5a of the InP window layer 5 to the inside of the InGaAs diffusion concentration distribution control layer 4 in the depth direction, and decreases to $5 \times 10^{16}/cm^3$ or less at a deeper position in the diffusion concentration distribution control layer 4. The Zn concentration distribution near the pn-junction 15 shows a graded type junction.

As for a one-dimensional or two-dimensional arrangement of the light-receiving elements 10, that is, the light-receiving element array shown in FIG. 3, adjacent light-receiving elements are separated from each other by performing selective diffusion of Zn (diffusion that is two-dimensionally limited so that a diffused portion is disposed inside a peripheral portion of each light-receiving element) without performing mesa etching for element separation. Specifically, the Zn selective diffusion region 6 constitutes a main portion of one light-receiving element 10 and forms one pixel, and regions where Zn does not diffuse separate respective pixels from each other. Therefore, the light-receiving element array does not suffer from, for example, crystal damage caused by mesa etching, and thus a dark current can be suppressed.

PTL 7 describes a concern that, in the case where a pn-junction is formed by selective diffusion of an impurity, the distance between elements cannot be decreased to a certain dimension or less because the impurity diffuses not only in the depth direction but also in the lateral direction (the direction orthogonal to the depth direction). However, according to an experimental result of selective diffusion of Zn, it was confirmed that, in the structure in which the InP window layer 5 is arranged on the top surface and the InGaAs diffusion concentration distribution control layer 4 is arranged under the InP window layer 5, the area of the diffusion in the lateral direction is substantially the same as or smaller than the area of the diffusion in the depth direction. That is, in selective diffusion of Zn, although Zn diffuses in the lateral direction so that the diameter of a diffusion region is larger than the diameter of an opening of a mask pattern, the degree of lateral diffusion is small and the region is only slightly expanded from the opening of the mask pattern, as schematically shown in, for example, FIGS. 1 and 3.

FIG. 4 is a cross-sectional view of a light-receiving element 110 of Reference Example 1 that is different from the present invention. The light-receiving element 110 of Reference Example 1 has the following stacked structure. (InP substrate 101/InP or InGaAs buffer layer 102/absorption layer 103 having
(GaInNAs/GaAsSb) Multiquantum Well Structure/InP Window Layer 105)

This stacked structure differs from the stacked structure of the embodiment of the present invention in that the diffusion concentration distribution control layer is not provided. That is, the absorption layer 103 having the multiquantum well structure is disposed directly under the InP window layer 105.

When the diffusion concentration distribution control layer is not provided, as shown in FIG. 5, for example, as for the Zn concentration distribution, a high concentration region extends to the absorption layer 103 having the multiquantum well structure. Specifically, a high-concentration impurity region with a concentration of $1\times10^{18}/cm^3$, which exceeds $5\times10^{16}/cm^3$, is formed in the multiquantum well structure. When a high-concentration impurity is introduced in the multiquantum well structure, the structure is broken, and the dark current significantly increases. In order to prevent such a high-concentration impurity region from being formed in the multiquantum well structure, the diffusion concentration distribution control layer is formed, and selective diffusion is then performed.

However, there is a possibility for realizing the following ideas regarding the selective diffusion of Zn.
(1) The time required for introduction by diffusion is limited to be short so that a high-concentration region does not reach the multiquantum well structure 103.
(2) The thickness of the InP window layer 105 is increased so that the InP window layer 105 has the function of the diffusion concentration distribution control layer.

FIG. 6 is a cross-sectional view showing a light-receiving element 110 of Reference Example 2 for examining the cases of (1) and (2) described above. The light-receiving element 110 of Reference Example 2 has a stacked structure substantially the same as that of the light-receiving element of Reference Example 1, but the thickness of an InP window layer 105 is larger than that of Reference Example 1. The light-receiving element 110 of Reference Example 2 corresponds to the case of (2) above, but can also be used for examining the case of (1) above. In the stacked structure shown in FIG. 6, selective diffusion is performed so that a high-concentration region of Zn is not formed in the multiquantum well structure 103. Consequently, a Zn concentration distribution shown in FIG. 7 is obtained. In the case of the Zn concentration distribution shown in FIG. 7, in the InP window layer 105, the Zn concentration drastically decreases from a high concentration to a low concentration, and a low-concentration impurity region with a concentration of about $1\times10^{16}/cm^3$ is formed in the InP window layer 105 at the absorption layer side.

When such a low-concentration impurity region with a concentration of about $1\times10^{16}/cm^3$ is formed in the InP window layer 105, the electrical resistance in the region increases, thereby decreasing the response time, as repeatedly described above. Accordingly, the function of the diffusion concentration distribution control layer cannot be provided to a material having a bandgap energy that is large enough to form the window layer, specifically, to the InP window layer 105, which is composed of such a typical material. This applies to both the cases of (1) and (2) above. Accordingly, a material having a bandgap energy corresponding to that of InP or less, specifically, a material that satisfies a bandgap energy of less than 1.34 eV is preferably used as the diffusion concentration control layer. That is, it is necessary to use a material, such as InGaAs, in which a decrease in the electrical conductivity is relatively small and an increase in the electrical resistance is relatively small even in a low-concentration impurity region.

(Embodiment 2 Structure of Imaging Device for Gas Monitoring)

FIG. 8 is a view showing the outline of an imaging device (light-receiving element array) for gas monitoring according to Embodiment 2 of the present invention. Optical members such as a lens for focusing on a gas in a predetermined range are omitted. FIG. 9 is a view illustrating the light-receiving element array of the imaging device. FIG. 10 is a view showing a single light-receiving element in the light-receiving element array 50 shown in FIG. 9. In FIG. 8, in the imaging device 70, light-receiving elements 10 formed on a common InP substrate 51 are epi-side down mounted so that the epitaxial layer side of the light-receiving elements 10 face a multiplexer 71 having a function of a mounting substrate. A p-side electrode 11 that is electrically connected to a p-type region 6 of an epitaxial layer of each of the light-receiving elements 10 and an n-side electrode 12 provided on the common n-type InP substrate 51 (1) are connected to the multiplexer 71 and send electrical signals to the multiplexer 71. The multiplexer 71 receives the electrical signals from each of the light-receiving elements and performs a process for forming a whole image in the predetermined range in which focusing on the gas has been performed. The n-side electrode 12 and the p-side electrode 11 are electrically connected to the multiplexer 71 via solder bumps 12b and 11b, respectively. Incident light enters through an anti-reflection (AR) film 35 formed on the reverse face of the InP substrate 51 and is received in a pn-junction 15 which is a boundary face between the p-type region 6 and an absorption layer 3. The p-type region 6 is introduced from an opening of a Zn diffusion mask 36 that is composed of SiN and that also functions as a protective film. The Zn diffusion mask pattern 36 is left as it is together with a SiON film pattern 43 functioning as a protective film and provided on the mask pattern 36. The structures of the light-receiving element array and each of the light-receiving elements will now be described in detail with reference to FIGS. 9 and 10, respectively.

In FIG. 9, light-receiving elements 10 of a light-receiving element array 50 are provided on a common InP substrate 51 (1). Current signals generated by receiving light in a short wave infrared (SWIR) band in each of the light-receiving elements are sent to a multiplexer 71, which also functions as a mounting substrate, and undergo a process for forming an image, as described above. The number of pixels is changed by changing the size and the pitch of each of the light-receiving elements and the size of the array. The light-receiving element array 50 shown in FIG. 9 has 90,000 pixels. The light-receiving element 10 shown in FIG. 10 includes a plurality of epitaxial films formed on an InP substrate 1. A diffusion mask 36 for introducing a p-type impurity, the diffusion mask 36 having been used in forming a p-type region 6, is left in the light-receiving element 10. A p-portion electrode 11 is connected to the p-type region 6, and is connected to, for example, wiring of a mounting substrate such as the multiplexer 71 via a solder bump or the like.

FIG. 11 is a cross-sectional view illustrating a light-receiving element that is epi-side up mounted, which is different from the epi-side down light-receiving element shown in FIG. 8. In the present invention, the light-receiving element in the imaging device may be epi-side down mounted or epi-side up mounted. In this light-receiving element 10, from the bottom, an n-type InP buffer layer 2, an absorption layer 3, a diffusion concentration distribution control layer 4, an InP window layer 5, a diffusion mask 36, and an AR film 35 are sequentially disposed on an n-type InP substrate 1. A p-type region 6 is formed so as to extend from the InP window layer 5 to a pn-junction 15 in the absorption layer 3 through the diffusion concentration distribution control layer 4. In addition, an n-side electrode 12 is disposed on the reverse face of the n-type InP substrate. A p-side electrode 11 is disposed on the surface of the InP window layer 5 of the p-type region 6 and is electrically connected to a wiring electrode 27. In this embodiment, the absorption layer 3 receives light having a wavelength in the range of 1.0 to 3.0 μm. Specifically, the absorption layer 3 is formed of the above-described type-II multiquantum well structure.

The light-receiving element shown in FIG. 11 is epi-side up mounted as described above. Light is incident from the epitaxial layer side, i.e., the InP window layer 5 side. The light-receiving element of this embodiment may be epi-side up mounted or epi-side down mounted as describe above. As shown in FIG. 12, the light-receiving element 10 may be epi-side down mounted, and light may be incident from the reverse face side of the InP substrate 1. In the case of the epi-side down mounted light-receiving element 10 shown in FIG. 12, an AR film 35 is provided on the reverse face of the InP substrate 1. A diffusion concentration control layer 4, an InP window layer 5, a p-side electrode 11, and a SiN diffusion mask 36 that also functions as a protective film are provided as in the case of the epi-side up mounting. In the epi-side down mounting shown in FIG. 12, InP constituting the InP substrate and the like is transparent to light in the SWIR band. Accordingly, the light in the SWIR band reaches a pn-junction 15 of an absorption layer 3 without being absorbed. Also in the structure shown in FIG. 12, the absorption layer is formed of the above-described type-II multiquantum well structure. This also applies to embodiments of the present invention described below unless otherwise stated.

As shown in FIG. 11, the p-side electrode 11 and the n-side electrode 12 may be arranged at positions facing each other with the InP substrate 1 therebetween. Alternatively, as shown in FIG. 12, the p-side electrode 11 and the n-side electrode 12 may be arranged at positions on the same side of the InP substrate 1. In the structure shown in FIG. 12, each of the light-receiving elements 10 of the light-receiving element array 50 shown in FIG. 9 is electrically connected to an integrated circuit by flip-chip mounting. In the light-receiving elements having the structures shown in FIGS. 11 and 12, light incident on the pn-junction 15 is absorbed to generate current signals. Each of the current signals is converted to an image of one pixel through the integrated circuit, as described above.

The InP substrate 1 is preferably an off-angle substrate which is tilted at 5 to 20 degrees from (100) in the [111] direction or the [11-1] direction. More preferably, the substrate is tilted at 10 to 15 degrees from (100) in the [111] direction or the [11-1] direction. By using such a substrate having a large off-angle, it is possible to obtain an n-type InP buffer layer 2, an absorption layer 3 having a type-II quantum well structure, an InGaAs diffusion concentration distribution control layer 4, and an InP window layer 5, all of which have a low defect density and good crystal quality. As a result, an absorption layer in which a dark current is suppressed and the number of dark spots is small can be obtained. Accordingly, it is possible to obtain an absorption layer that is capable of markedly improving the performance of a device that receives faint cosmic light in the SWIR band to acquire an image. That is, the operation of the light-receiving element formed using the above-mentioned off-angle substrate is particularly useful for improving the quality of an imaging device that receives cosmic light to acquire an image.

The above-mentioned large off-angle of an InP substrate has not been proposed to date, and the above advantage due to the use of such an InP substrate has been confirmed for the first time by the inventors of the present invention. The large off-angle of an InP substrate is an important factor in the case where an epitaxial film having a good crystal quality is grown on the InP substrate. For example, in the case where an absorption layer 3 having the above-described quantum well structure, the absorption layer 3 being supposed to be able to emit and receive light in a very long-wavelength range, contains a nitrogen (N)-containing compound semiconductor, for example, GaInNAs, in reality, the absorption layer 3 cannot be formed as a satisfactory epitaxial layer that can withstand practical use, unless an InP substrate having such a large off-angle is used. That is, a nitrogen-containing compound semiconductor, for example, GaInNAs cannot be formed into an absorption layer in which a dark current is suppressed and the number of dark spots is reduced, unless such an InP substrate having the above large off-angle is used. Consequently, it is impossible to obtain a sharp image using faint cosmic light in the SWIR band. Not only GaInNAs cited as an example above, but also GaInNAsP and GaInNAsSb are common in that the above-mentioned range of a large off-angle of the InP substrate is necessary in order to obtain a good crystal quality.

Each of the light-receiving elements 10 shown in FIGS. 11 and 12 includes the InGaAs diffusion concentration control layer 4 and the InP window layer 5 that are disposed so as to cover the absorption layer 3. Since a lattice parameter of the absorption layer 3 is the same as that of the InP substrate 1, the InGaAs diffusion concentration control layer 4 and InP window layer 5, which can reliably reduce the dark current, can be formed on the absorption layer 3. Consequently, the dark current can be suppressed to improve reliability of the element.

(Embodiment 3: Gas Monitoring Device (1)—Monitoring Device of Long-Term Degradation of OF Cable—)

FIG. 13 is a view showing a gas monitoring device 100 according to Embodiment 3 of the present invention. This gas monitoring device 100 monitors long-term degradation of an OF cable used for transmission of electrical power or the like. As shown in FIG. 14, the gas monitoring device 100 detects gas components present in gas-in-oil separation cells 40 provided in the OF cable. FIG. 15 is a view illustrating a hydrogen sensor 45 in a waveguide in the gas monitoring device 100. Before the structure of the gas monitoring device 100 is described with reference to FIGS. 13 to 15, a description will be made of a reason why long-term degradation can be monitored by detecting gas components contained in the gas-in-oil separation cell 40 of the OF cable.

FIG. 16 is a graph showing the concentrations of methane $CH_4$ and acetylene $C_2H_2$, which are gas components contained in the gas-in-oil separation cell 40. The approximate degree of degradation can be determined by detecting the concentrations of methane and acetylene. In FIG. 16, the results are divided into four groups of A, B, C, and D on the basis of the concentrations of methane and acetylene. Immediately after the analysis of the gas components, OF cables were disassembled to examine the degree of the degradation. The following relationships were observed between the results and the above four groups.

Group A: Breaking of cable portion etc.
Group B: Discoloration of core etc.
Group C: Corona discharge crater in connecting portion etc.
Group D: Some connecting sheets were slightly changed to a waxy state, but many normal connecting sheets were also observed.

The results show that the degree of long-term degradation increases from Group D to Group A. In order to examine the long-term degradation with higher accuracy, it is necessary to detect hydrogen $H_2$, ethene $C_2H_4$, ethane $C_2H_6$, and carbon monoxide CO in addition to methane $CH_4$ and acetylene $C_2H_2$. To detect these gas components including hydrogen $H_2$, the devices shown in FIGS. 13 to 15 are used.

Peak wavelengths of absorption spectra of the above gas components in the near-infrared region are as follows.
Acetylene $C_2H_2$: 1.5201 μm
Carbon monoxide CO: 1.5688 μm
Ethene $C_2H_4$: 1.6245 μm
Methane $CH_4$: 1.6456 μm
Ethane $C_2H_6$: 1.6816 μm Hydrogen $H_2$ has no absorption spectrum in the near-infrared region because hydrogen is composed of diatomic molecules and a change in the dipole moment does not occur. Therefore, in order to detect hydrogen, the hydrogen sensor 45 whose color is changed by contacting hydrogen to adsorb hydrogen is arranged so that the hydrogen sensor 45 is exposed in the gas cell 40 and a light propagation path passes through the hydrogen sensor 45. Light in the near-infrared region in the light propagation path is attenuated by the coloring of the hydrogen sensor due to hydrogen adsorption. Accordingly, since the amount of transmitted light in the near-infrared region changes depending on the magnitude of the hydrogen concentration, hydrogen can be detected by this change in the amount of light.

In FIG. 13, as a light source 73, for example, a halogen lamp that emits light having wavelengths in the range of near-infrared region to the visible region can be used. The light is guided from a light guide end 81*a* to an optical fiber, and divided into measurement light and reference light by an optical branching unit 88*a*. The measurement light is guided to an optical fiber 81. The reference light is guided to an optical fiber 7*c* and enters an optical path switch 8. The measurement light is emitted from an emission end of the optical fiber 81 to the gas-in-oil separation cell or the gas cell 40. In the gas cell 40, the above gas components containing hydrogen are mixed because of secular change. Light that has been subjected to absorption corresponding to the above peak wavelengths in the near-infrared region, the absorption being other than absorption of hydrogen, propagates from the light guide end through an optical fiber 82. Light including information of absorption of the gas components and propagating through the optical fiber 82 is branched with an optical branching unit 88*b*. One of the branched light components is incident on the optical path switch 8 while including the information. Another branched light component propagates through the hydrogen sensor 45 whose color has been changed by hydrogen, passes through an optical fiber 7*b*, and is incident on the optical path switch 8.

FIG. 15 is a view showing the hydrogen sensor 45. The hydrogen sensor 45 includes, as main components, a substrate 45*a* composed of $LiNbO_3$, a light propagation path 45*b* formed by introducing titanium Ti into the substrate by thermal diffusion, a $WO_3$ thin film 45*c* formed by depositing $WO_3$ on the light propagation path 45*b* by vacuum evaporation, and a Pd thin film 45*d* formed by depositing Pd on the $WO_3$ thin film 45*c* by sputtering. Both ends of the light propagation path 45*b* are connected to the optical fiber 7*b* (refer to FIG. 13). When this hydrogen sensor 45 is placed in the gas cell 40 containing hydrogen, the Pd thin film 45*d* functions as a catalyst and the $WO_3$ thin film 45*c* is colored. As a result, an attenuation rate of evanescent light propagating through the light propagation path 45*b* increases, and the amount of transmitted light in the near-infrared region attenuates. This change in the amount of transmitted light includes inforftmation of the hydrogen concentration.

Referring to FIG. 13, the three optical fibers 7*a*, 7*b*, and 7*c* are connected to the optical path switch 8. For example, when light passing through the optical fiber 7*a* is passed through the optical path switch 8, light including information of gas components other than hydrogen is emitted from an emission end 82*b*. This light is collimated by a lens and incident on a diffraction grating 91. The diffraction grating 91 spectrally separates the light and emits the separated light components having respective wavelengths to the light-receiving element array 50 in accordance with the emission angle. The light-receiving element array 50 may be a one-dimensional array or a two-dimensional array. Each of the light-receiving elements in the array corresponds to a wavelength in advance in accordance with the position thereof. Consequently, an absorption spectrum of gas components except for hydrogen, the spectrum including base noise, can be obtained. Such a measurement of a spectrum is performed for not only the light passing through the optical fiber 7*a*, but also the reference light passing through the optical fiber 7*c* and the hydrogen sensor-transmitted light passing through the optical fiber 7*b*. The switching of the optical fibers 7*a*, 7*b*, and 7*c* is performed by the optical path switch 8. The order of the measurement of the optical fibers is not particularly limited. For example, the measurement of spectra may be performed as follows. (1) First, a spectrum of the light passing through the hydrogen sensor 45 provided in the gas-in-oil separation cell 40 and passing through the optical fiber 7*c* is determined. This measurement of the light passing through the hydrogen sensor 45 is performed both before and after the coloring due to hydrogen. Next, (2) a spectrum of the reference light of the optical fiber 7*c* is obtained. (3) A spectrum of the light passing through the gas-in-oil separation cell 40 and then passing through the optical fiber 7*a* is obtained.

The concentrations of respective gas components can be determined by determining the intensities at absorption peak wavelengths of the gas components described above on the basis of the above spectra. As for hydrogen, an appropriate wavelength in the near-infrared region is determined in advance, and the hydrogen concentration can be determined on the basis of a change in the intensity at the wavelength between before and after the coloring of the hydrogen sensor 45.

As for the hydrogen concentration, the degree of coloring of the hydrogen sensor 45 may be directly measured using visible light. In such a case, light including the visible range that is located at the short wavelength side of the near-infrared region is absorbed by the InP substrate. In a configuration in which the light-receiving elements 10 are arranged in a line, as shown in FIG. 11, it is preferable to use a light-receiving element 10 in which the top of an epitaxial layer functions as a light-incident surface (epi-side up mounting) and the InP substrate is located at the mounting side. With regard to a one-dimensional array provided on a common InP substrate, it is easy to form the structure of the light-receiving element 10 shown in FIG. 11 on a single common InP substrate. However, with regard to the structure of a two-dimensional array, it is difficult to provide wiring extending from respective p-side electrodes so that the wiring does not disturb light. For this reason, with regard to a two-dimensional array 50 on a common InP substrate, as shown in FIG. 17, it is preferable to use a structure in which the top of an epitaxial layer is located at the mounting side (epi-side down mounting) and the buffer layer 2 side or the absorption layer 3 side functions as the light-incident side. Preferably, the InP substrate is removed or the thickness of the InP substrate is reduced to a dimension substantially the same as the thickness of the absorption layer 3 or less. In FIG. 17, the InP substrate has been removed. In this light-receiving element array 50, a common n-side electrode 12 is connected to an electrode pad 12c for a ground potential, the electrode pad 12c being provided on a complementary metal-oxide semiconductor (CMOS) 71, with a bonding wire 12w therebetween. Furthermore, each of the p-side electrodes 11 is connected to a corresponding electrode pad 11c provided in a protective film 43. In this light-receiving element array 50, light-receiving elements can be two-dimensionally arranged on a common InP substrate. Thus, light in the visible range can be received with good sensitivity, and the coloring of the hydrogen sensor 9 can be directly monitored. The light-receiving element array 50 or the imaging device 40 shown in FIG. 17 will be described also in a modification of this embodiment of the present invention and Embodiment 4 described below.

According to a known technique (PTL 2), in the secular change monitor of an OF cable, five laser light sources adjusted to the absorption peak wavelengths of respective gas components are arranged to determine the concentration of the respective gas components. In addition, the laser light sources are modulated, and the hydrogen concentration is determined by using the modulated light. In the gas monitoring device 100 shown in FIG. 13, the above-mentioned five laser light sources are not necessary, and a modulator is also not necessary. As a result, the economical efficiency can be markedly improved, and the monitoring device can be significantly simplified. Accordingly, the need for maintenance to prevent breakdown decreases, and the frequency of the maintenance can be reduced.

FIGS. 18 and 19 are views showing a modification of Embodiment 3 of the present invention. This modification is common to the gas monitoring device 100 shown in FIG. 13 etc. in that when a gas component having an absorption band in the near-infrared region and hydrogen, which has no absorption band, coexist, the hydrogen concentration and the concentration of the other gas component are determined. This modification differs from the above-described gas monitoring device 100 in that no optical fiber passes through a hydrogen sensor 45, and light propagating through a gas passes through the hydrogen sensor 45 to measure a spectrum of the light passing through the hydrogen sensor 45. Specifically, as shown in FIG. 17, the hydrogen sensor 45 includes a transparent glass substrate 45g and a catalyst thin film 45f. For example, Pt, Pd, PdWO$_3$, or PtWO$_3$ can be used as the catalyst. Light guided from a light guide end 81a to a gas cell 40 through an optical fiber 81 and a lens 87 passes through a gas in which gas components are mixed and the hydrogen sensor 45. The light is then guided to an optical fiber 82 through another lens 87. The subsequent path is the same as the optical fiber 7a shown in FIG. 13.

In a known technique (PTL 1), the oscillation frequency of a laser light source is adjusted to an absorption band of a hydrogen sensor 45, and a wavelength range of a double frequency emitted when the laser light source is modulated is adjusted to the absorption peak wavelengths of hydrocarbon gases. According to this method, the hydrogen concentration and the concentration of the other gas component can be determined without affecting each other. In the case of the known device, a modulator, a Peltier device for temperature control, a phase sensitive detector, and other components are necessary. In contrast, the light monitoring device shown in FIGS. 18 and 19 has the same configuration of the device shown in FIG. 13, which is very simple. Also in the device shown in FIGS. 18 and 19, the light-receiving element shown in FIG. 11 or a one-dimensional array thereof, or the light-receiving element array 50 shown in FIG. 17 may be used as the light-receiving element 10 or the light-receiving element array 50. The use of these light-receiving elements in which the absorption in the short wavelength range is decreased is rather preferable from the standpoint of examining a change in the coloring of the hydrogen sensor 45.

(Embodiment 4: Gas Monitoring Device (2)—Combustion State Monitoring Device—)

FIG. 20 is a view showing a gas monitoring device or a combustion state monitoring device 100c according to Embodiment 4 of the present invention. This combustion state monitoring device 100c is a device configured to diagnose a combustion state of a flame in a combustion furnace, in which a spectrum of flame light guided from a plurality of optical probes P1, P2, etc. that receive the flame light is measured to perform a diagnosis with high accuracy. For the purpose of environmental pollution protection, it is desired that nitrogen oxides, soot, and carbon monoxide be not generated in a combustion device such as a boiler. In order to form a combustion state, a flame in which a fuel and air are appropriately mixed is formed in a combustion furnace. It is necessary that an extremely high-temperature region be not formed and an extremely low-temperature region be not formed in the combustion furnace by performing this appropriate mixing. An example of a device for monitoring such a combustion state is a device configured to detect a flame emission spectrum and to diagnose the combustion state on the basis of a characteristic of this spectrum. The combustion state monitoring device according to this embodiment corresponds to such a device.

In the combustion state monitoring device 100c shown in FIG. 20, a plurality of probes P1, P2, and Pn (or light guide ends 82a) are attached to a furnace wall of a boiler so that flame light is guided to a plurality of optical fibers 82. The optical fibers 82 are connected to an optical path switch 8. Only an optical fiber of an optical path selected by the optical path switch 8 turns to the ON state, and light passes through the optical fiber. The light of the optical path in the ON state is emitted from an emission end 82b of the optical fiber to a lens 87. The light collimated by the lens 87 is diffracted by a diffraction grating 91, and light of each wavelength is received by a light-receiving element array 50. The light-receiving element array 50 may be a one-dimensional array or a two-dimensional array formed on a common InP substrate, or an array in which individual light-receiving elements 10 are arranged. With regard to this light-receiving element array 50, as shown in FIG. 21, an emission spectrum of soot extends to the visible range. Accordingly, as described above, when individual light-receiving elements 10 are arranged in a line, preferably, as shown in FIG. 11, the top of an epitaxial layer functions as a light-incident surface (epi-side up mounting) and the InP substrate is located at the mounting side. With regard to a one-dimensional array, it is easy to produce the structure in which the light-receiving elements 10 shown in FIG. 11 are one-dimensionally arranged on a single common InP substrate. On the other hand, in order to obtain a two-dimensional array 50 on a common InP substrate, as shown in FIG. 17, the top of an epitaxial layer is located at the mounting side and the buffer layer 2 side or the absorption layer 3 side functions as the light-incident side (epi-side down mounting). Preferably, the InP substrate is removed or the thickness of the InP substrate is reduced. Thus, light in the visible region can be received with high sensitivity, and an emission spectrum of soot can be monitored with high sensitivity.

According to a known technique (PTL 3), a plurality of interference filters are attached to a turn table, and a double-layer element in which a silicon photodiode and a PbS photoconductive element are stacked is used as a light-receiving element. The number of double-layer light-receiving elements required is the same as the number of interference filters, and the light-receiving elements are also attached to the turn table. The combustion state monitoring device 100c shown in FIG. 20 does not require the turn table, the interference filters, or the double-layer light-receiving elements, and can be significantly simplified as compared with the existing device. This significant simplification improves the measurement accuracy, reduces the frequency of the maintenance necessary for the combustion state monitoring device, and reduces the production cost of the device.

(Embodiment 5: Gas Monitoring Device (3)—Temperature Distribution Measuring Device in Combustion of Garbage (Temperature Camera)—)

FIG. 22 shows a temperature distribution measuring device 100d for obtaining a temperature distribution of garbage in a combustor. FIG. 23 is a view showing a temperature distribution imaging device 55. In the combustor, carbon or hydrocarbons are present in an agglomerated state, and thus are not present in the form suitable for a fuel. Accordingly, the amount of soot is small, and a large amount of moisture is present. FIG. 24 shows a near-infrared spectrum in a combustor, and emission spectrum wavelengths $\lambda_2$ and $\lambda_3$ of water are noticeably observed. In this embodiment, the concentration and the temperature of water are monitored by using a phenomenon that an emission spectrum of water changes depending on the temperature and in combination with an absorption spectrum of water shown in FIG. 25. In FIGS. 25, (K1) and (K2) were measured using cuvette cells with a size of 10 mm and 1 mm, respectively. Since the intensity of the emission spectrum is also proportional to the concentration of water, it is difficult to perform measurement with high accuracy using the only two emission peak wavelengths. Therefore, the absorption spectrum is also used.

In the temperature distribution imaging device 55, an interference filter 55a is important. The interference filter 55a is a filter having transmission wavelengths at the above-mentioned emission peak wavelengths $\lambda_2$ and $\lambda_3$ of water, and a plurality of absorption peak wavelengths. For example, regarding the absorption peak wavelengths, as shown in FIG. 25, the absorption spectrum has two sharp peaks M2 and M3 in the near-infrared region. The interference filter 55a is configured to pass light components having these wavelengths. Accordingly, the interference filter 55a includes total four types of filters or filters having total four transmission wavelengths in combination with the above-mentioned two emission peak wavelengths. It is preferable to provide an automatic selection mechanism that automatically selects these four types of interference filters by an external operation. An optical system 55c such as a lens also preferably includes an automatic focusing mechanism that automatically performs focusing. For example, an image of garbage or a slightly upper portion of the garbage is captured with respect to light components having four wavelengths in accordance with the above four types of interference filters. Thus, an image corresponding to the four wavelengths can be obtained.

The intensity of the light components at the above wavelengths may be determined in advance for air in which the water vapor temperature and the water vapor concentration are changed to determine a regression formula of the temperature. This temperature regression formula is stored in a microcomputer 85b of a control unit. By the above imaging, intensities of respective wavelengths can be obtained at each position. By using the above temperature regression formula, the temperature can be determined at each position. The combustion state of garbage can be detected with high accuracy by monitoring both the temperature and the concentration of water in this manner.

According to a known technique (PTL 4), a plurality of temperature sensors are arranged in a combustor. However, the number of temperature sensors can be reduced by arranging the device of this embodiment on an upper portion or the top of an incinerator.

(Embodiment 6: Gas Monitoring Device (4)—Device for Monitoring Impurities in Process Gas—)

FIG. 26 is a view showing a device 100e for monitoring impurities contained in a gas, the device 100e being a gas monitoring device according to Embodiment 6 of the present invention. This device is the device disclosed in NPL 2. A semiconductor laser having an emission wavelength around 1,371 µm (corresponding to M2 shown in FIG. 25) is used as a light source 73, and light is divided into two beams using a beam splitter 93 and a mirror 94. One of the beams is passed through a sample cell into which a process gas of a measurement target is introduced, and the other beam is used as a beam for cancel. Lock-in detection is performed for a measurement of light intensity in order to remove a direct-current noise component.

A difference between the device of this embodiment and the device disclosed in NPL 2 is the content of photodetectors (light-receiving elements) 10a and 10b. A germanium photodiode having a preamplifier is used in NPL 2, whereas the light-receiving element shown in FIG. 10 or FIG. 11 is used in this embodiment. Consequently, spectroscopy in the near-infrared region in which the dark current is low can be realized with high sensitivity. Furthermore, not only a single wavelength but also any of the absorption peak wavelengths shown in FIG. 25 can be selected. Accordingly, by preparing a semiconductor laser device corresponding to M1 to M3 in FIG. 25, the moisture concentration can be monitored at three wavelengths. Thus, the concentration of moisture, which is the most undesirable impurity in a process gas, can be monitored with higher accuracy.

EXAMPLE

Example Regarding Structure of Semiconductor Light-Receiving Element Array

To which degree the pixel pitch or the distance between elements of the light-receiving element array of the present invention can be decreased was examined by way of Example using the light-receiving element array shown in FIG. 27. The distance between light-receiving elements or the pixel pitch is the width of a masking portion of a SiN selective diffusion mask pattern 36, as shown in FIG. 27. After selective diffusion of Zn, a p-side electrode 11 made of AuZn and an n-side electrode 12 made of AuGeNi were formed. In the case of FIG. 3, since an Fe-doped semi-insulating substrate is used as the InP substrate 1, the n-side electrode 12 is provided on the buffer layer 2 containing an impurity at a high concentration. In the case where the n-type InP substrate is used as shown in FIG. 1, the n-side electrode may be provided on the reverse face of the substrate, or the n-side electrode may be provided on an n-type semiconductor layer (e.g., buffer layer 2) adjacent to the substrate on the top surface side of the substrate. In this Example, a reverse bias voltage of 5 V was applied between the p-side electrode 11 and the n-side electrode 12 of the light-receiving element array shown in FIG. 3, and the dark current was measured. Light-receiving element arrays having two types of the thickness of the InP window layer 5 of 0.6 µm and 1.6 µm and seven types of the distance between elements in the range of 3 to 20 µm were produced, and the dark current was measured. The thickness of the diffusion concentration distribution control layer 4 was 1 µm.

The results are shown in FIG. 28. Referring to FIG. 28, in the case where the InP window layer 5 has a small thickness of 0.6 µm, even when the distance between elements or the pixel pitch is reduced to 5 µm, the dark current can be suppressed to $1\times10^{-10}$ A (ampere). In the case where the InP window layer 5 has a thickness of 1.6 µm, diffusion of Zn expands in the lateral direction as described above. Therefore, unless the distance between elements exceeds 7 µm, the dark current cannot be suppressed to $1\times10^{-10}$ A. However, in this Example, it was confirmed that the distance between elements could be reduced to 5 µm by reducing the thickness of the InP window layer 5 to 0.6 µm and arranging the diffusion concentration distribution control layer.

The function of the diffusion concentration distribution control layer 4 was examined by analyzing a concentration distribution of Zn in the depth direction by SIMS. FIG. 29 shows the concentration distribution of Zn in the depth direction. Referring to FIG. 29 at the boundary face between the InGaAs diffusion concentration distribution control layer 4 and the absorption layer 3, the peak value of pile-up of Zn is suppressed to $5\times10^{16}$ cm$^3$ or less. Accordingly, in a pn-junction formed at a crossing position (indicated by a circle in the figure) of the background of the n-type carrier concentration of the absorption layer 3 and the Zn concentration, the Zn concentration can be reliably reduced, and degradation of the crystal quality or the like can be prevented. In addition, by arranging this diffusion concentration distribution control layer 4, it becomes possible for the multiquantum well structure of the absorption layer to achieve the original function thereof.

Embodiments and Example of the present invention have been described above. The embodiments and Example of the present invention disclosed above are only illustrative, and the scope of the present invention is not limited to these embodiments of the invention. It is to be understood that the scope of the present invention is defined by the description of Claims and includes equivalence of the description in Claims and all modifications within the scope of Claims.

Industrial Applicability

According to the present invention, an examination with high accuracy can be performed by an outstanding improvement of the performance of InP-based PDs, as compared with existing devices for examining the food quality. Thus, the present invention can be conducive to reliability of foods. In addition, the present invention can bring a revolution such as the realization of identification of brand foods.

REFERENCE SIGNS LIST

Figure 1:
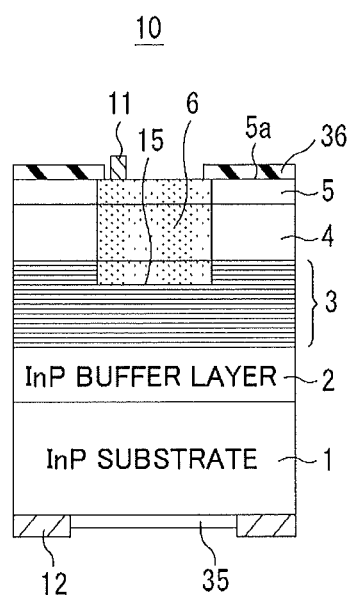
FIG. 1 is a cross-sectional view showing a light-receiving element according to Embodiment 1 of the present invention.
Figure 2:
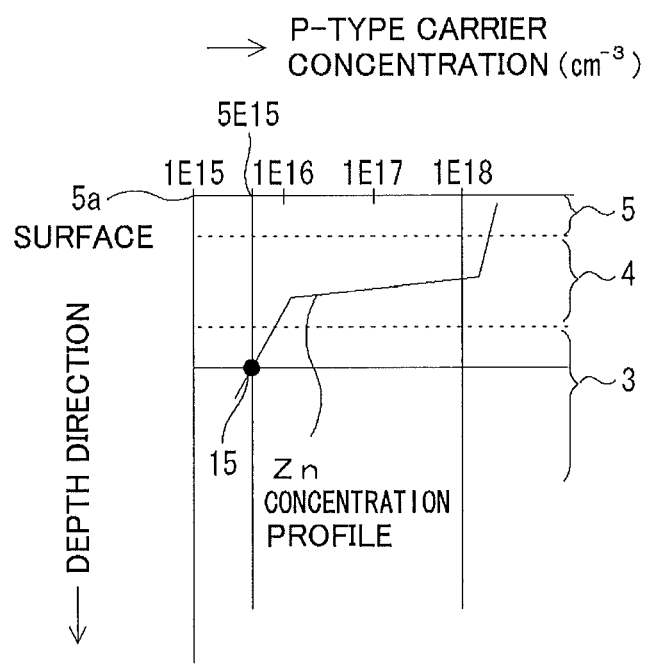
FIG. 2 is a drawing showing a Zn concentration distribution in the light-receiving element shown in FIG. 1.
Figure 3:
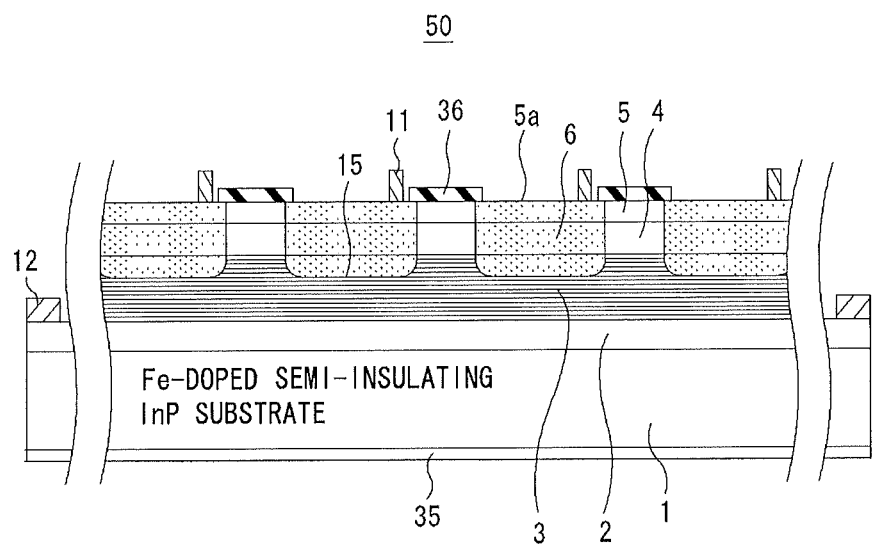
FIG. 3 is a cross-sectional view showing a light-receiving element array according to Embodiment 1 of the present invention.
Figure 4:
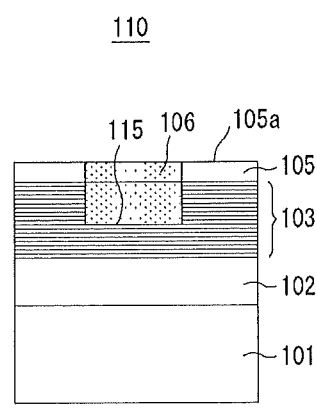
FIG. 4 is a cross-sectional view of a light-receiving element of Reference Example 1 that is different from the present invention.
Figure 5:
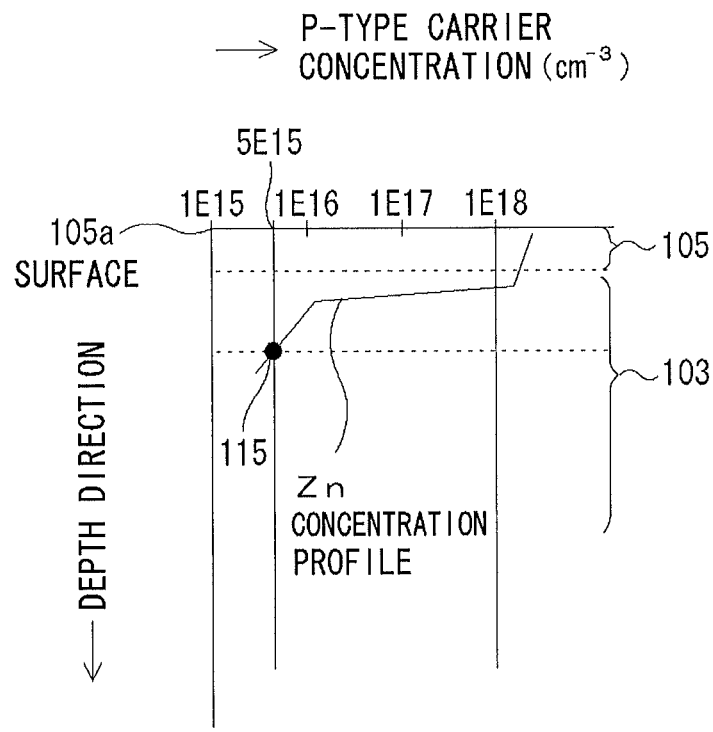
FIG. 5 is a drawing showing a Zn concentration distribution in the light-receiving element shown in FIG. 4.
Figure 6:
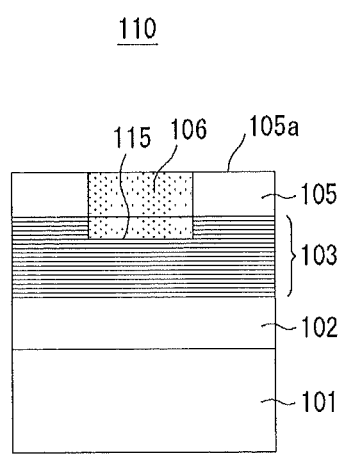
FIG. 6 is a cross-sectional view of a light-receiving element of Reference Example 2 that is different from the present invention.
Figure 7:
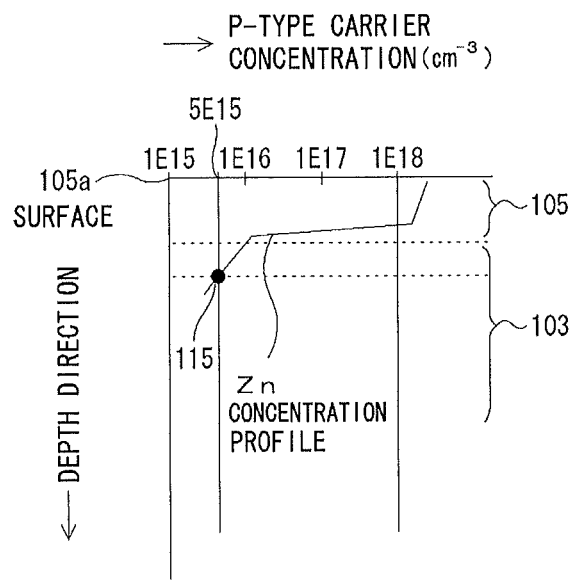
FIG. 7 is a drawing showing a Zn concentration distribution in the light-receiving element shown in FIG. 6.
Figure 8:
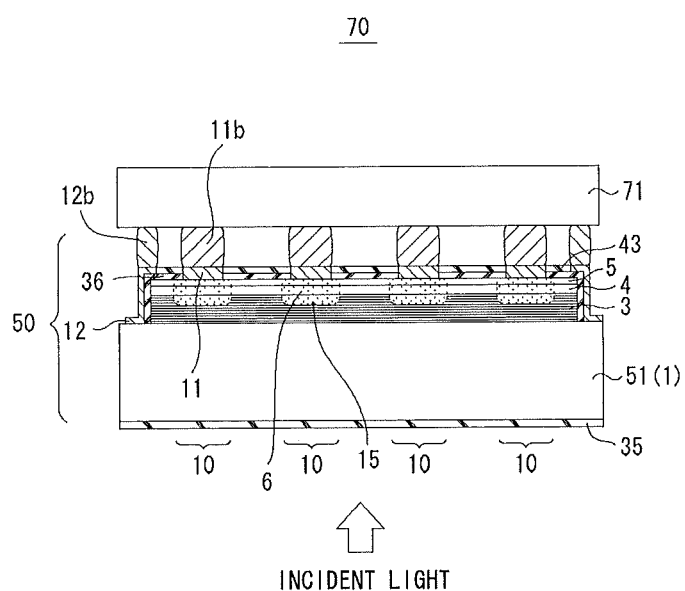
FIG. 8 is a view showing the outline of an imaging device according to Embodiment 2 of the present invention.
Figure 9:
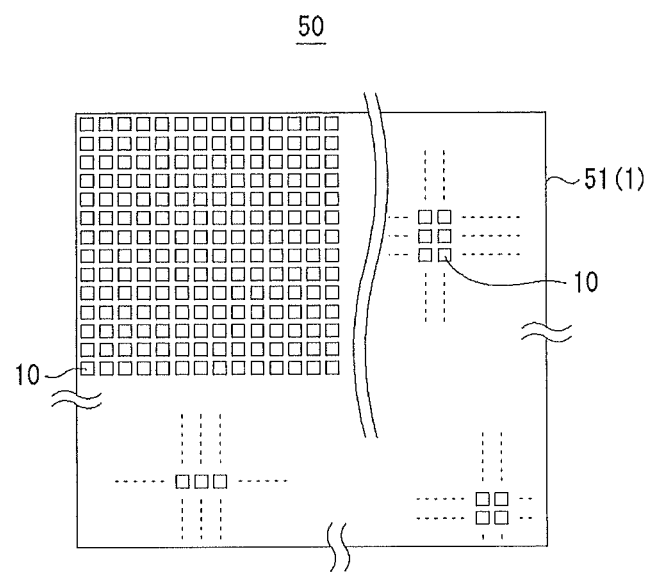
FIG. 9 is a view showing a light-receiving element array of the imaging device shown in FIG. 8.
Figure 10:
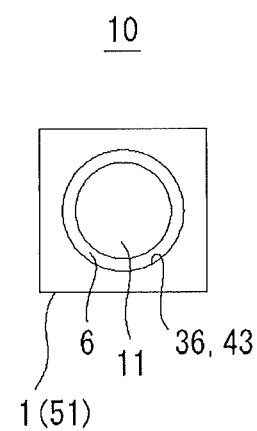
FIG. 10 is a view showing one light-receiving element in the light-receiving element array shown in FIG. 9.
Figure 11:
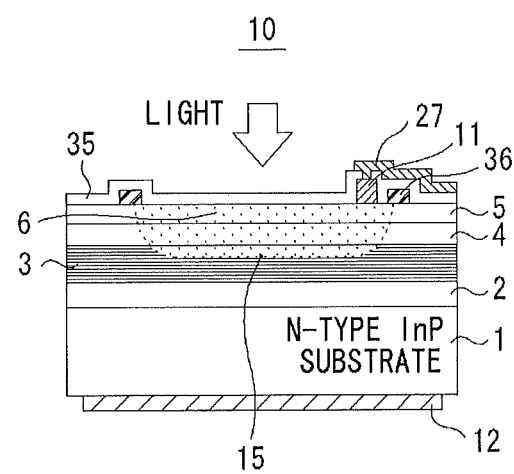
FIG. 11 is a cross-sectional view of a light-receiving element of epi-side up mounting.
Figure 12:
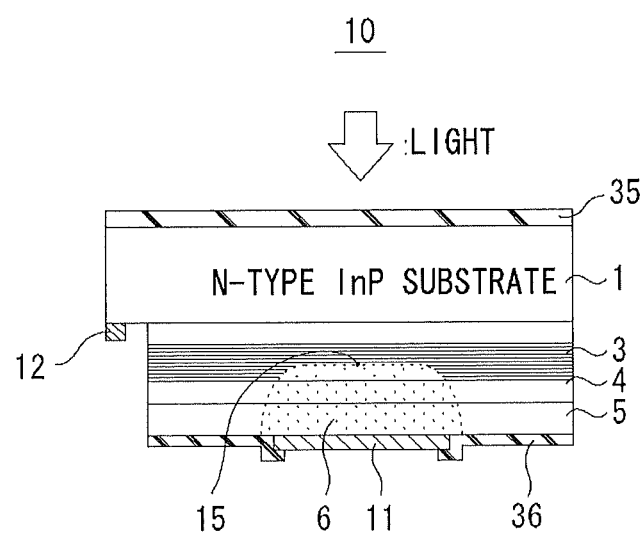
FIG. 12 is a cross-sectional view of a light-receiving element of epi-side down (flip-chip) mounting.
Figure 13:
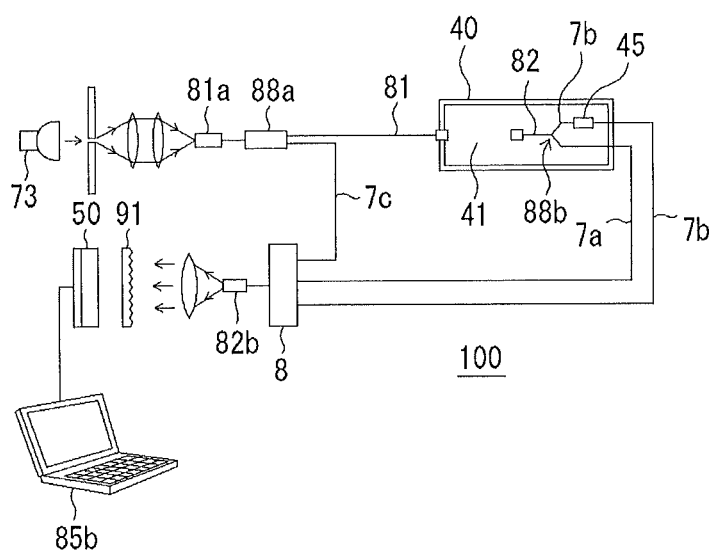
FIG. 13 is a view showing a gas monitoring device (1) according to Embodiment 3 of the present invention.
Figure 14:
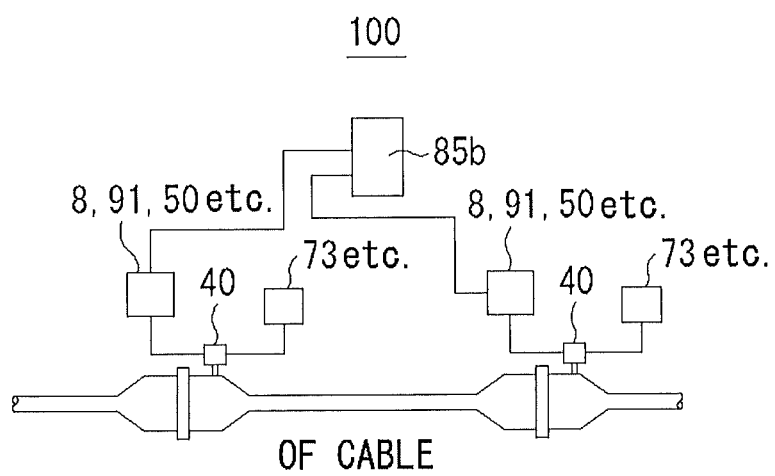
FIG. 14 is a view showing a state in which the gas monitoring device (1) shown in FIG. 13 is attached to a gas-in-oil separation cell of an OF cable.
Figure 15:
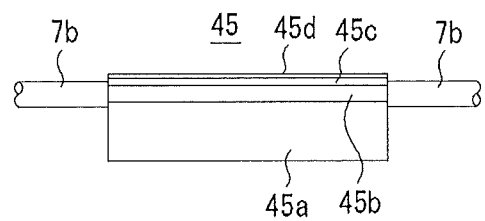
FIG. 15 is a view showing a hydrogen sensor and an optical fiber disposed through the hydrogen sensor.
Figure 16:
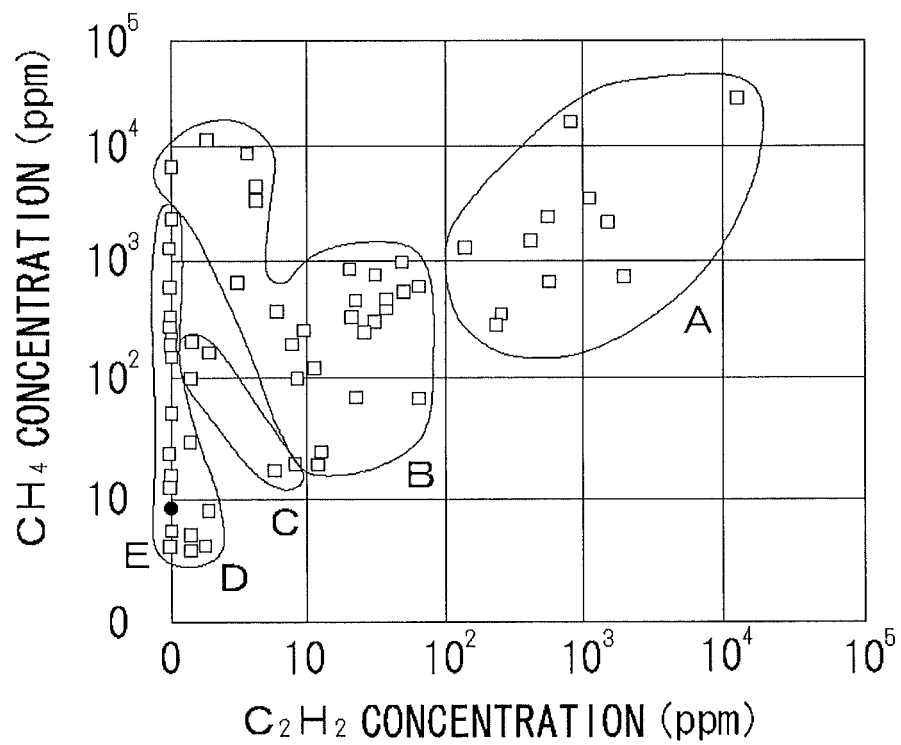
FIG. 16 is a graph showing an example of a relationship between a long-term degradation level of an OF cable and gas components.
Figure 17:
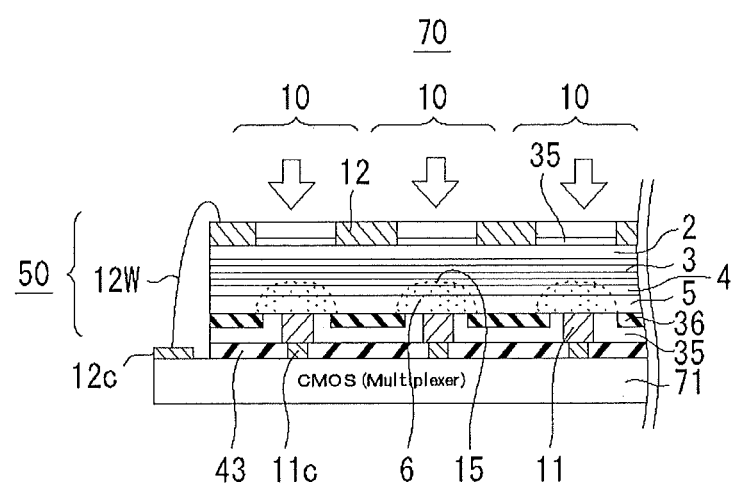
FIG. 17 is a view showing an example of a light-receiving element of the present invention suitable for a case where sensitivity in the visible range is necessary besides sensitivity in the near-infra red region.
Figure 18:
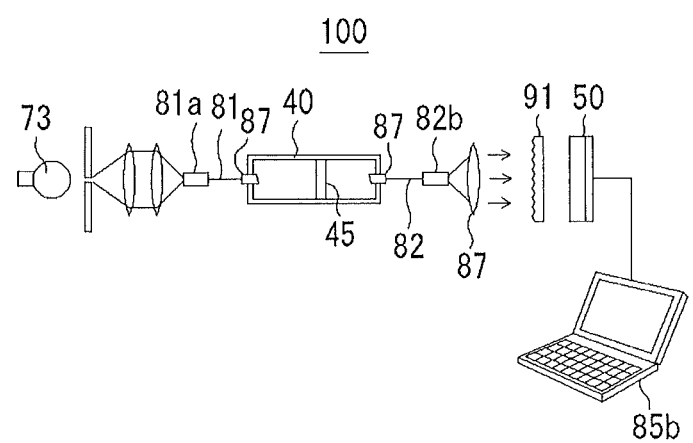
FIG. 18 is a view showing a modification of the gas monitoring device (1) shown in FIG. 13.
Figure 19:
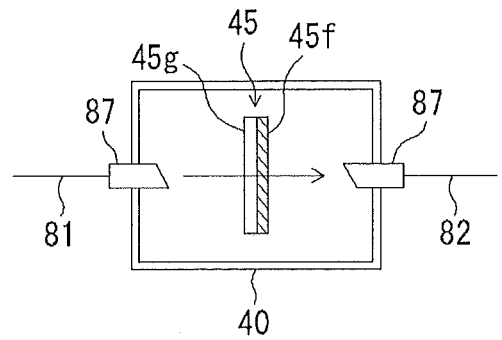
FIG. 19 is a view showing a hydrogen sensor used in FIG. 19.
Figure 20:
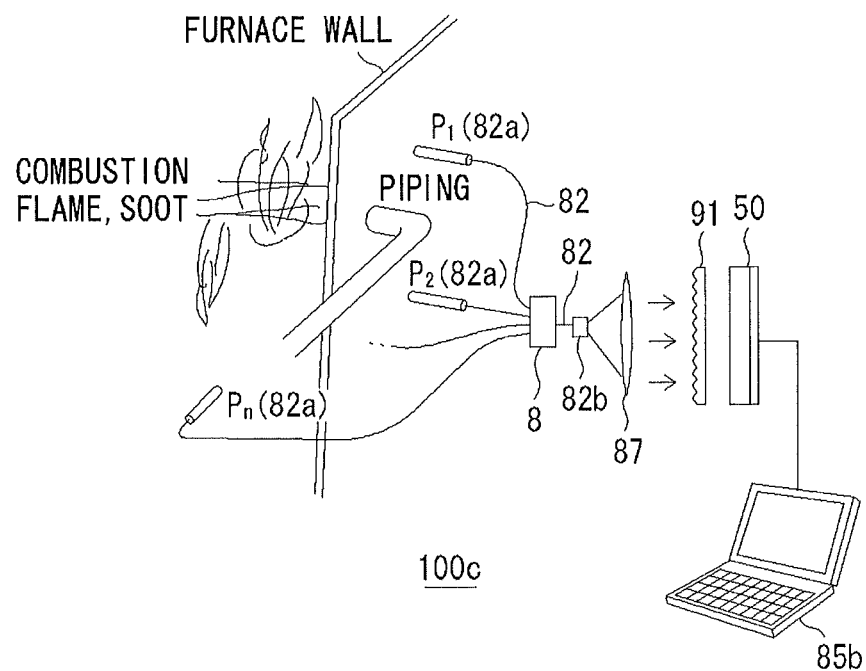
FIG. 20 is a view showing a combustion state monitoring device of a gas monitoring device (2) according to Embodiment 4 of the present invention.
Figure 21:
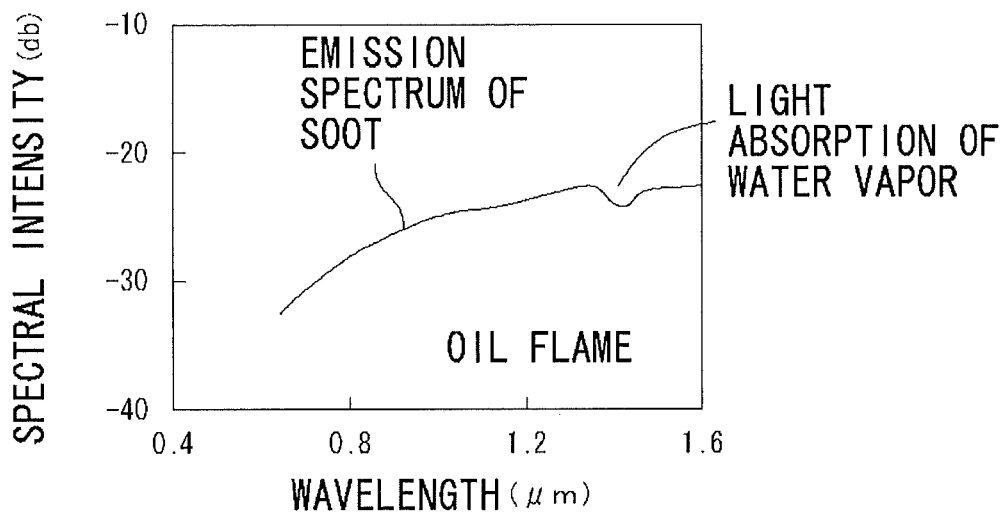
FIG. 21 is a view showing an example of a spectrum of flame light.
Figure 22:
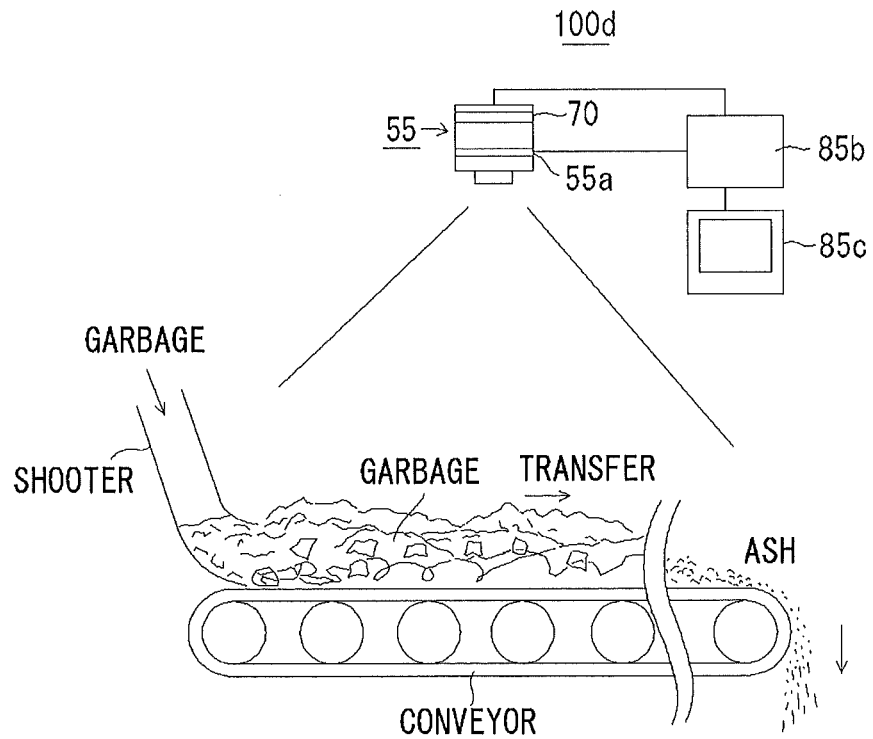
FIG. 22 is a view showing a temperature distribution measuring device of a gas monitoring device (3) according to Embodiment 5 of the present invention.
Figure 23:
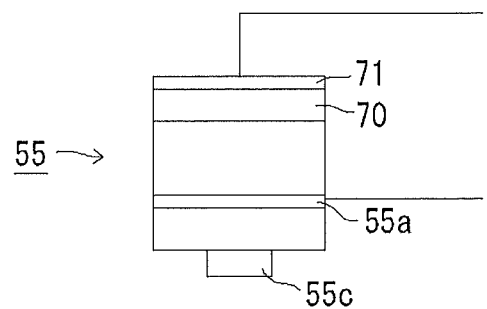
FIG. 23 is a view showing an imaging device in the gas monitoring device (3) shown in FIG. 22.
Figure 24:
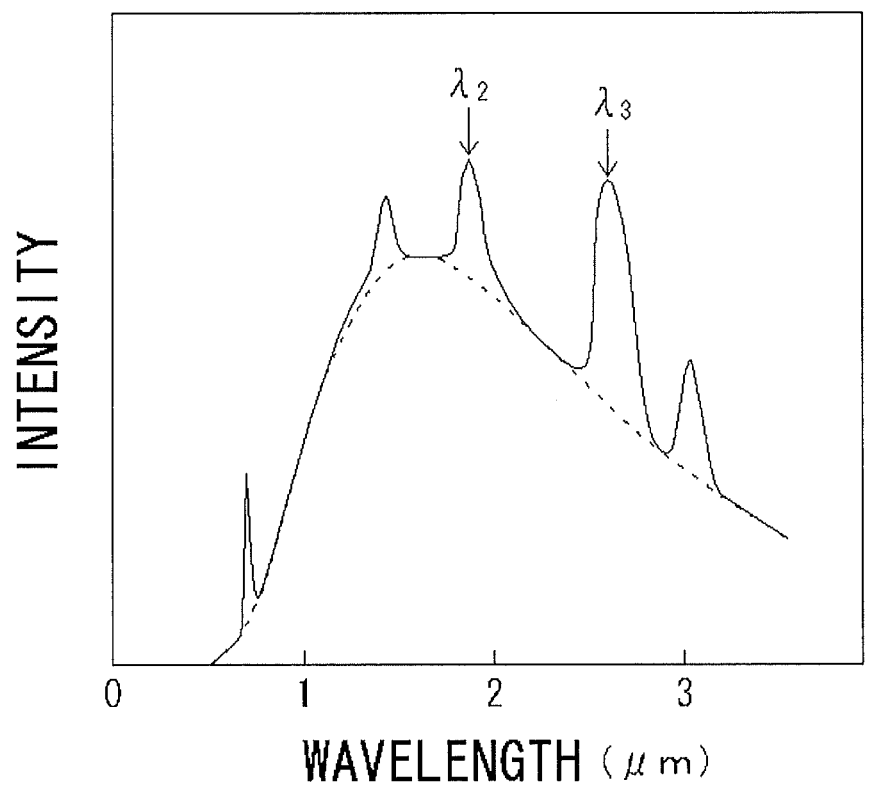
FIG. 24 is a graph showing an emission spectrum of water for explaining the principle of the gas monitoring device (3) shown in FIG. 22.
Figure 25:
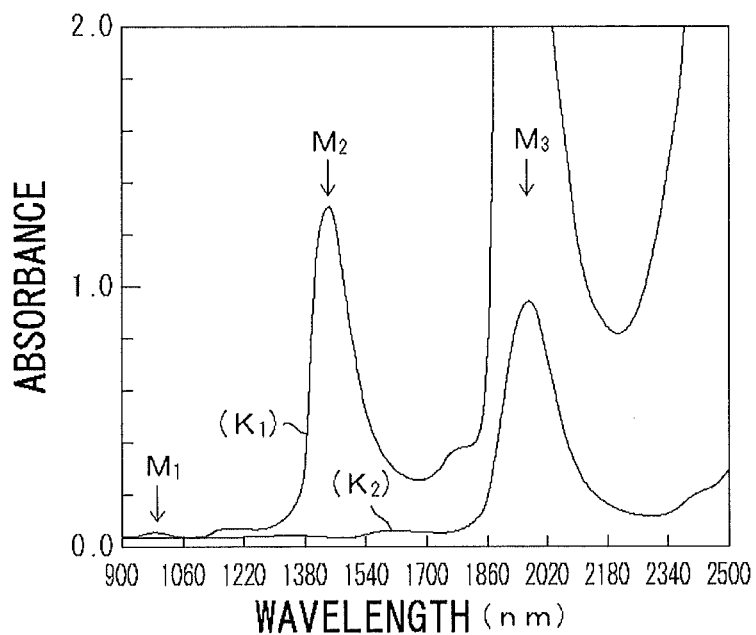
FIG. 25 is a graph showing an absorption spectrum of water for explaining the principle of the gas monitoring device (3) shown in FIG. 22.
Figure 26:
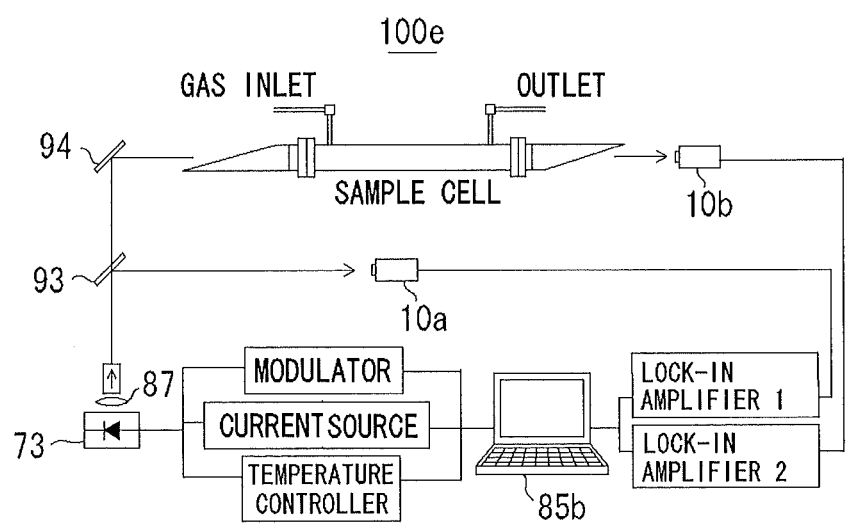
FIG. 26 is a view showing an impurity monitoring device of a gas monitoring device (4) according to Embodiment 6 of the present invention.
Figure 27:
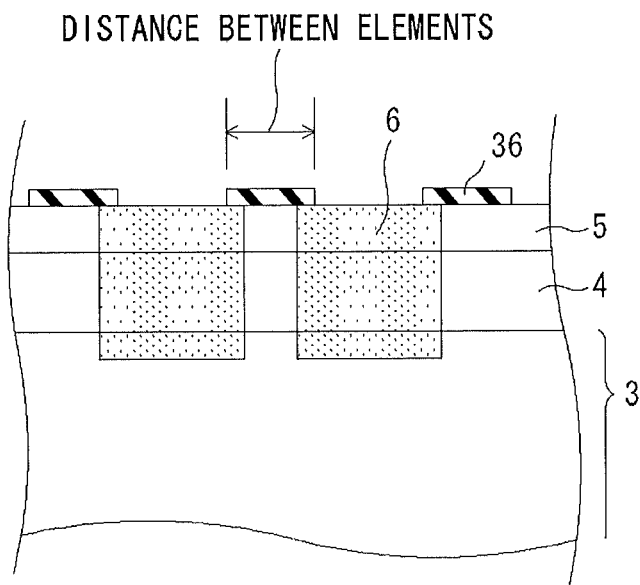
FIG. 27 is a partial cross-sectional view of a light-receiving element array used in Example.
Figure 28:
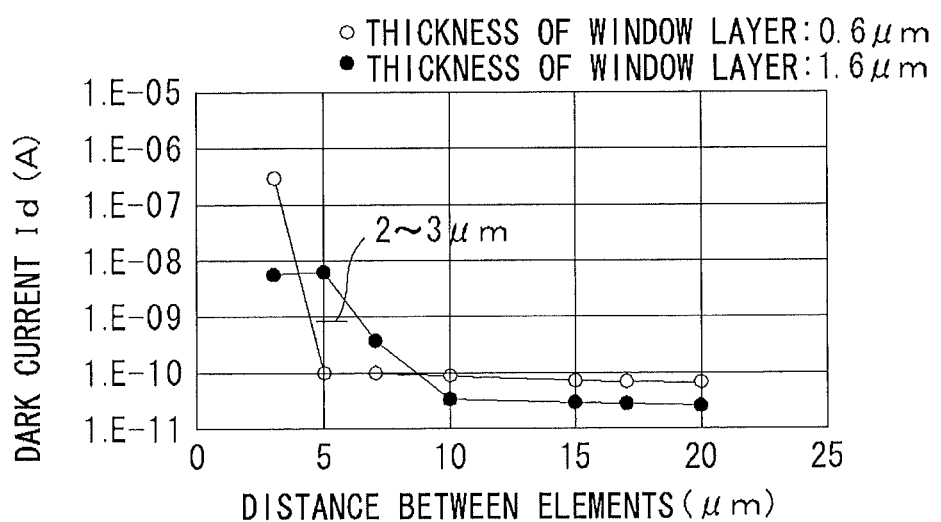
FIG. 28 is a graph showing a relationship between the distance between elements and a dark current measured in Example.
Figure 29:
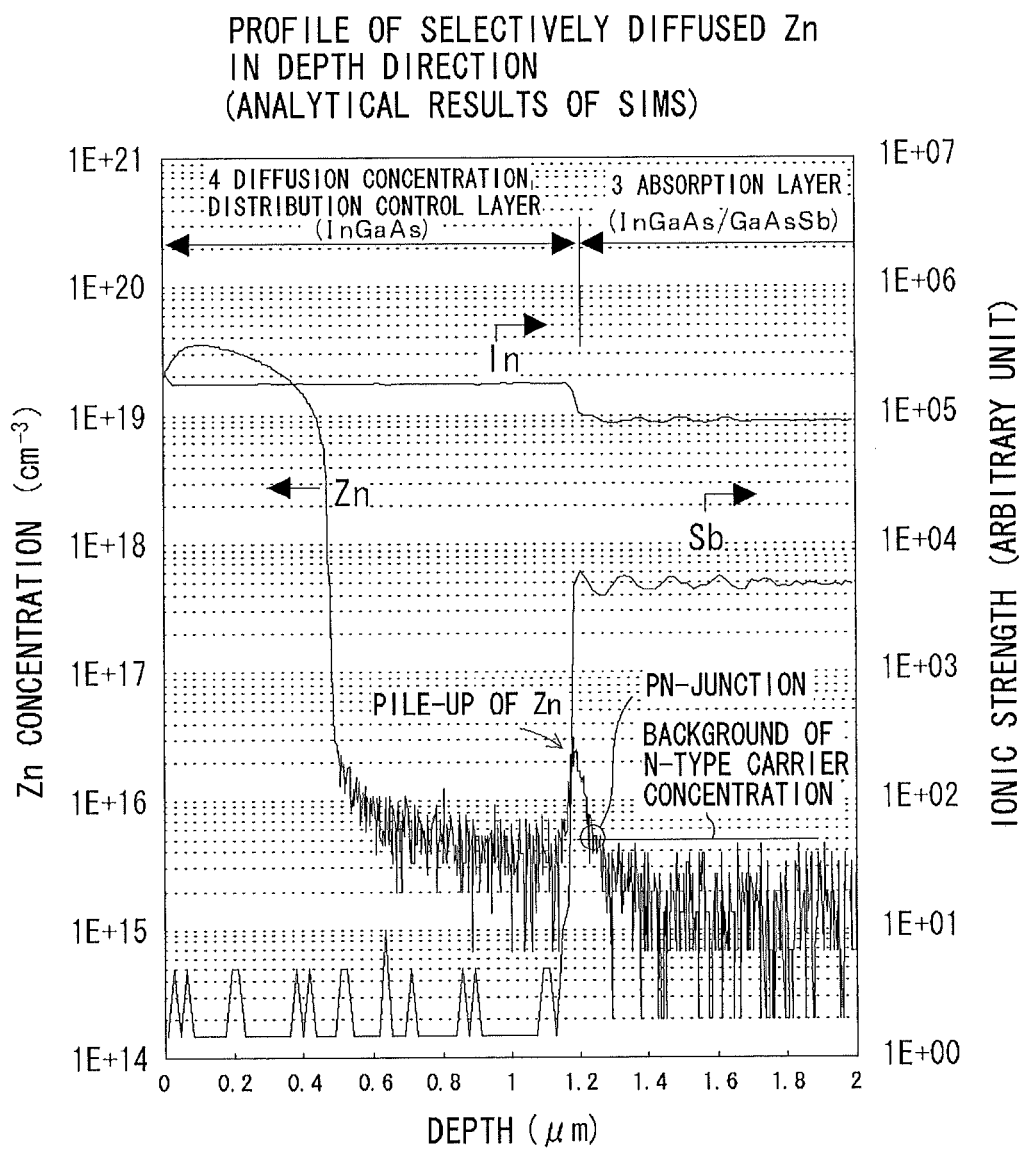
FIG. 29 is a graph showing a concentration distribution of Zn in the depth direction in Example.

1 InP substrate, 2 buffer layer, 3 absorption layer having a multiquantum well structure, 4 diffusion concentration distribution control layer, 5 InP window layer, 5a surface of window layer, 6 p-type region, 7a, 7b, and 7c optical fiber, 10, 10a, and 10b light-receiving element, 11 p-side electrode, 12 n-side electrode, 12b solder bump, 12c electrode pad, 12w bonding wire, 15 pn-junction, 35 anti-reflection film, 36 selective diffusion mask pattern, 27 wiring electrode, 40 gas cell (gas-in-oil separation cell), 41 gas, 43 protective film, 45 hydrogen sensor, 45a substrate, 45b light propagation path (optical fiber), 45c $WO_3$ thin film, 45d Pd thin film, 45f catalyst thin film, 45g substrate, 50 light-receiving element array, 51 InP substrate, 55 imaging device, 55a filter portion, 55c optical system, 70 imaging device, 71 multiplexer (mounting substrate), 73 light source, 81 optical fiber, 81a light guide end, 81b emission end, 82 optical fiber, 83 probe, 85 control unit, 85b microcomputer (operation unit, CPU), 85c display unit (output device), 87 lens, 91 spectroscope (diffraction grating), 93 beam splitter, 94 mirror, 100 gas monitoring device, 100c combustion state monitoring device, 100d temperature distribution measuring device, 100e impurity monitoring device

What is claimed is:

1. A gas monitoring device for monitoring a gas using light in the near-infrared region with a wavelength range of 3 μm or less, the gas monitoring device comprising:
   a light-receiving element that receives light in the near-infrared region,
   wherein the light-receiving element includes an absorption layer formed on an InP substrate and having a multiquantum well structure,
   the absorption layer has a bandgap wavelength of 1.8 μm or more and 3 μm or less; and
   a diffusion concentration distribution control layer is disposed on a surface side of the absorption layer, the surface side being opposite the InP substrate,
   the diffusion concentration distribution control layer has a bandgap smaller than that of InP,
   in the light-receiving element, a pn-junction is formed by selectively diffusing an impurity element through the diffusion concentration distribution control layer so as to reach the absorption layer,
   the concentration of the impurity element in the absorption layer is $5 \times 10^{16}/cm^3$ or less, and
   the light-receiving element receives light from the gas, the light having at least one wavelength of 3 μm or less, to detect a gas component and the like contained in the gas.

2. The gas monitoring device according to claim 1, wherein, in the diffusion concentration distribution control layer, the concentration of the impurity element decreases from a high concentration of about $1 \times 10^{18}/cm^3$ or more on the side opposite the absorption layer to $5 \times 10^{16}/cm^3$ or less on the absorption layer side.

3. A combustion state monitoring device comprising the gas monitoring device according to claim 2, wherein a combustion state of a fuel or garbage is monitored.

4. A secular change monitoring device comprising the gas monitoring device according to claim 2, wherein a gas component that is generated with a secular change in an instrument is monitored.

5. An impurity concentration monitoring device comprising the gas monitoring device according to claim 2, wherein the concentration of a gas component of impurities contained in a gas introduced from the outside is monitored.

6. The gas monitoring device according to claim 1, wherein the absorption layer has a type II quantum well structure.

7. The gas monitoring device according to claim 6, wherein the absorption layer has a multiquantum well structure composed of (InGaAs/GaAsSb) or a multiquantum well structure composed of (GaInNAs(P, Sb)/GaAsSb).

8. A combustion state monitoring device comprising the gas monitoring device according to claim 6, wherein a combustion state of a fuel or garbage is monitored.

9. A secular change monitoring device comprising the gas monitoring device according to claim 6, wherein a gas component that is generated with a secular change in an instrument is monitored.

10. An impurity concentration monitoring device comprising the gas monitoring device according to claim 6, wherein the concentration of a gas component of impurities contained in a gas introduced from the outside is monitored.

11. The gas monitoring device according to claim 1, wherein the InP substrate is an off-angle substrate which is tilted at 5° to 20° from (100) in the [111] direction or the [11-1] direction.

12. The gas monitoring device according to claim 1, wherein the impurity element is zinc (Zn), and the diffusion concentration distribution control layer is composed of InGaAs.

13. The gas monitoring device according to claim 1, further comprising an InP window layer disposed on the diffusion concentration distribution control layer.

14. The gas monitoring device according to claim 1, wherein, in any two of the InP substrate, the absorption layer, and the diffusion concentration distribution control layer, lattice matching (|Δa/a|: where a represents a lattice parameter and Δa represents a difference in the lattice parameter between the two) is 0.002 or less.

15. The gas monitoring device according to claim 1, wherein a plurality of the light-receiving elements are one-dimensionally or two-dimensionally arrayed.

16. The gas monitoring device according to claim 1, further comprising an imaging device including a two-dimensional array of the light-receiving elements, wherein images of the concentration distribution and the temperature distribution of the gas component in a predetermined range in the gas are formed with the imaging device.

17. The gas monitoring device according to claim 1, wherein, in the light-receiving element, an epitaxial layer top side that is opposite the InP substrate side with the absorption layer therebetween functions as a light-incident surface, or the InP substrate side functions as the light-incident surface and the InP substrate is removed or the thickness of the InP substrate is reduced to the same thickness as that of the absorption layer or less.

18. A combustion state monitoring device comprising the gas monitoring device according to claim 1, wherein a combustion state of a fuel or garbage is monitored.

19. A secular change monitoring device comprising the gas monitoring device according to claim 1, wherein a gas component that is generated with a secular change in an instrument is monitored.

20. An impurity concentration monitoring device comprising the gas monitoring device according to claim 1, wherein the concentration of a gas component of impurities contained in a gas introduced from the outside is monitored.

* * * * *